United States Patent
Straehnz et al.

(10) Patent No.: US 8,740,919 B2
(45) Date of Patent: *Jun. 3, 2014

(54) DEVICES FOR DISPENSING SURGICAL FASTENERS INTO TISSUE WHILE SIMULTANEOUSLY GENERATING EXTERNAL MARKS THAT MIRROR THE NUMBER AND LOCATION OF THE DISPENSED SURGICAL FASTENERS

(75) Inventors: Jens-Peter Straehnz, Bielefeld (DE); Doug Souls, Andover, NJ (US); Michael Cardinale, Morristown, NJ (US); Brian Auer, Rathdrum, ID (US); Simon Cohn, Lebanon, NJ (US)

(73) Assignee: Ethicon, Inc., Somerville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/422,003

(22) Filed: Mar. 16, 2012

(65) Prior Publication Data

US 2013/0245681 A1    Sep. 19, 2013

(51) Int. Cl.
*A61B 17/10* (2006.01)

(52) U.S. Cl.
USPC ......................................................... 606/143

(58) Field of Classification Search
CPC ........... A61B 17/07207; A61B 17/064; A61B 2017/07214; A61B 2017/07271; A61B 17/068; A61B 2019/545
USPC ......... 606/139, 142, 143, 151, 213, 215, 219, 606/220; 227/175.1–182.1
See application file for complete search history.

(56) References Cited

U.S. PATENT DOCUMENTS

| | | | |
|---|---|---|---|
| 3,009,852 A | 11/1961 | Gruner | |
| 3,740,994 A | 6/1973 | DeCarlo, Jr. | |
| 3,812,859 A * | 5/1974 | Murphy et al. | ............... 606/117 |
| 4,180,197 A | 12/1979 | Raasch et al. | |
| 4,325,376 A | 4/1982 | Klieman et al. | |
| 4,471,780 A | 9/1984 | Menges et al. | |
| 4,478,220 A | 10/1984 | DiGiovanni et al. | |
| 4,921,326 A | 5/1990 | Wild et al. | |
| 4,924,864 A | 5/1990 | Danzig | |
| 5,174,487 A | 12/1992 | Rothfuss et al. | |
| 5,203,864 A | 4/1993 | Phillips | |
| 5,290,297 A | 3/1994 | Phillips | |
| 5,469,847 A | 11/1995 | Zinreich et al. | |
| 5,470,010 A | 11/1995 | Rothfuss et al. | |
| 5,582,616 A | 12/1996 | Bolduc et al. | |
| 5,601,573 A | 2/1997 | Fogelberg et al. | |
| 5,810,882 A | 9/1998 | Bolduc et al. | |
| 5,830,221 A | 11/1998 | Stein et al. | |
| 5,833,700 A | 11/1998 | Fogelberg et al. | |

(Continued)

*Primary Examiner* — Ryan Severson
*Assistant Examiner* — Katherine M Shi
(74) *Attorney, Agent, or Firm* — Doherty & Charney LLC

(57) ABSTRACT

A device dispenses surgical fasteners inside a body and generates marks outside the body indicating where the surgical fasteners have been dispensed inside the body. The device includes a first member having a surgical fastener dispenser opening, and a second member coupled with the first member, the second member having a distal end that opposes the surgical fastener dispenser opening. The device includes a marking assembly secured to the distal end of the second member. The marking assembly is moveable away from and toward the surgical fastener dispenser opening. The marking assembly is adapted for generating marks on an external surface that mirror the location of each surgical fastener dispensed from the surgical fastener dispenser opening. The device may include a clamp for compressing tissue between the marking assembly and the surgical fastener dispenser.

20 Claims, 23 Drawing Sheets

(56) References Cited

U.S. PATENT DOCUMENTS

| | | |
|---|---|---|
| 5,921,997 A | 7/1999 | Fogelberg et al. |
| 6,053,926 A | 4/2000 | Luers et al. |
| 6,160,870 A | 12/2000 | Jacobson |
| 6,419,680 B1 | 7/2002 | Cosman et al. |
| 6,425,900 B1 | 7/2002 | Knodel et al. |
| 6,712,859 B2 | 3/2004 | Rousseau et al. |
| 6,779,701 B2 | 8/2004 | Bailly |
| D538,851 S | 3/2007 | Sandel et al. |
| 7,442,167 B2 | 10/2008 | Dunki-Jacobs et al. |
| 7,615,065 B2 | 11/2009 | Priewe et al. |
| 8,518,055 B1 | 8/2013 | Cardinale et al. |
| 2002/0068947 A1 | 6/2002 | Kuhns et al. |
| 2006/0079910 A1 | 4/2006 | Tartaglia |
| 2007/0187456 A1 | 8/2007 | Viola et al. |
| 2008/0290135 A1* | 11/2008 | Mastri et al. ............... 227/179.1 |
| 2010/0137890 A1 | 6/2010 | Martinez et al. |
| 2010/0222791 A1* | 9/2010 | Stone et al. .................... 606/144 |
| 2010/0234687 A1 | 9/2010 | Azarbarzin et al. |
| 2010/0292710 A1 | 11/2010 | Daniel et al. |
| 2010/0292712 A1 | 11/2010 | Nering et al. |
| 2010/0292713 A1 | 11/2010 | Cohn et al. |
| 2010/0292715 A1 | 11/2010 | Nering et al. |
| 2010/0292717 A1 | 11/2010 | Petter-Puchner |
| 2010/0327042 A1 | 12/2010 | Amid et al. |
| 2011/0079627 A1 | 4/2011 | Cardinale et al. |
| 2011/0178536 A1* | 7/2011 | Kostrzewski ................ 606/144 |
| 2012/0059244 A1 | 3/2012 | McClelland et al. |
| 2012/0175401 A1 | 7/2012 | Bachman |
| 2013/0245642 A1 | 9/2013 | Souls et al. |

\* cited by examiner

FIG. 5
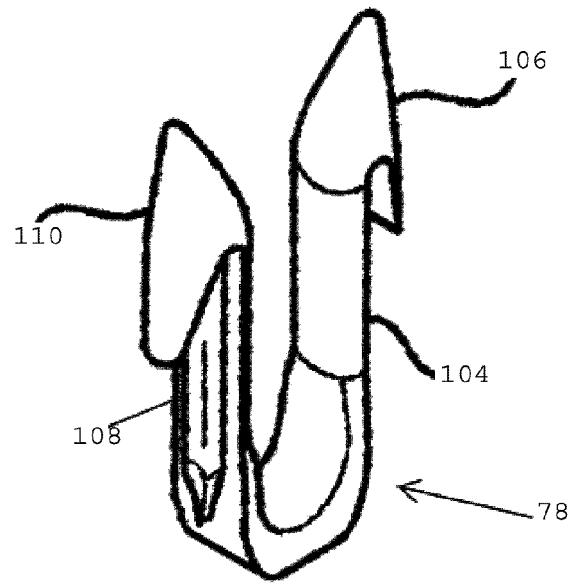
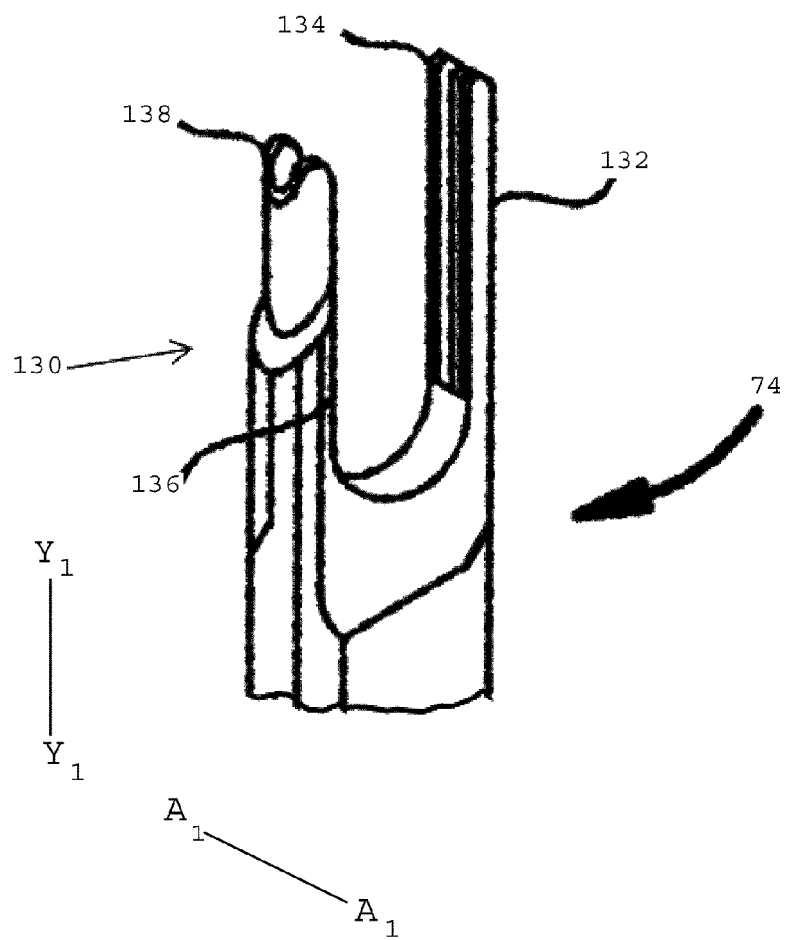

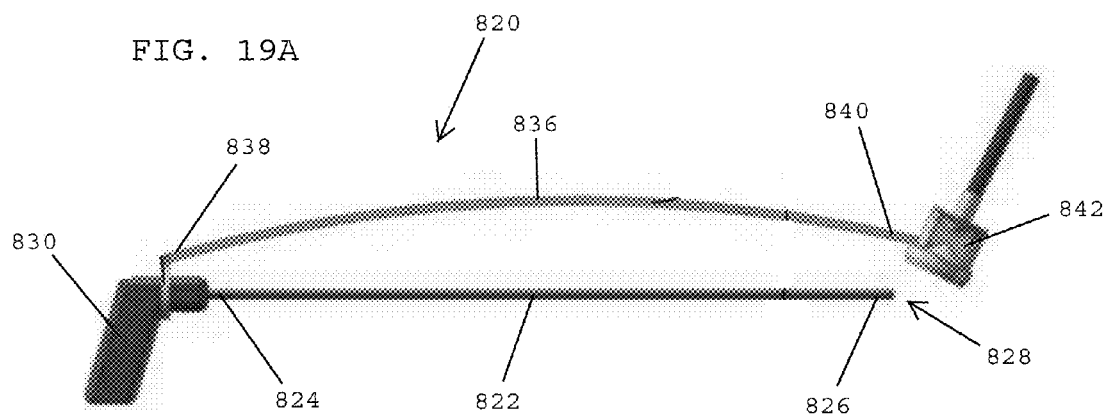
FIG. 19A
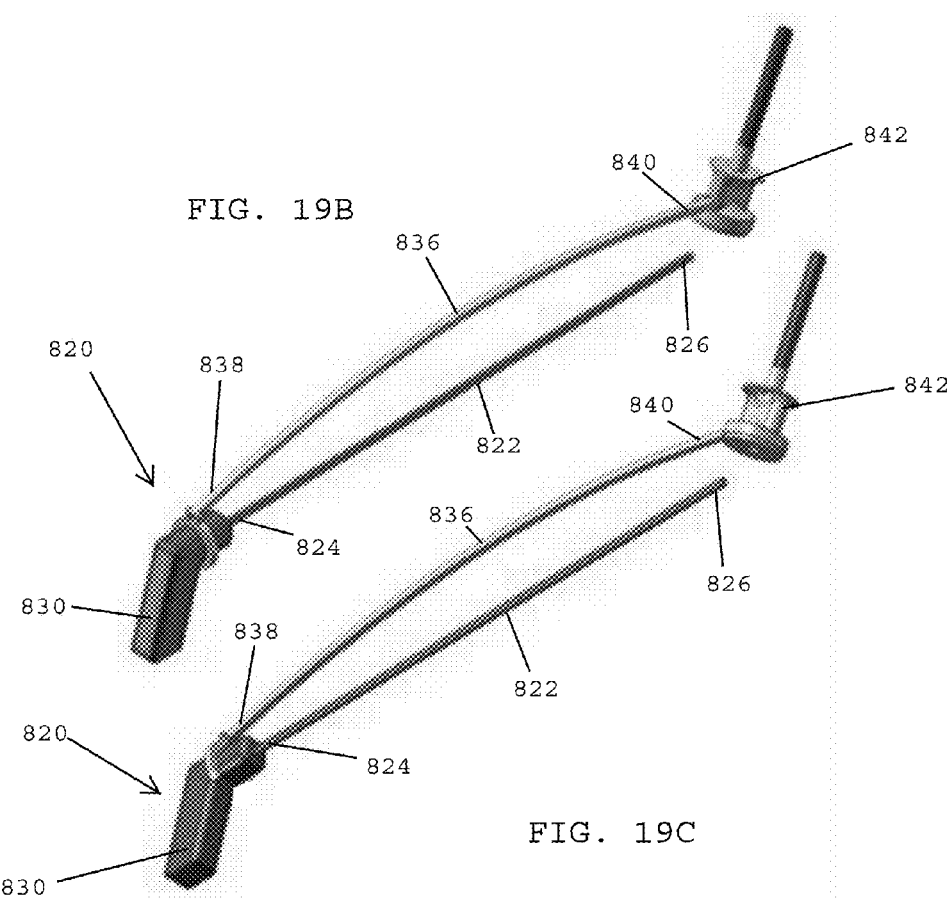
FIG. 19B
FIG. 19C

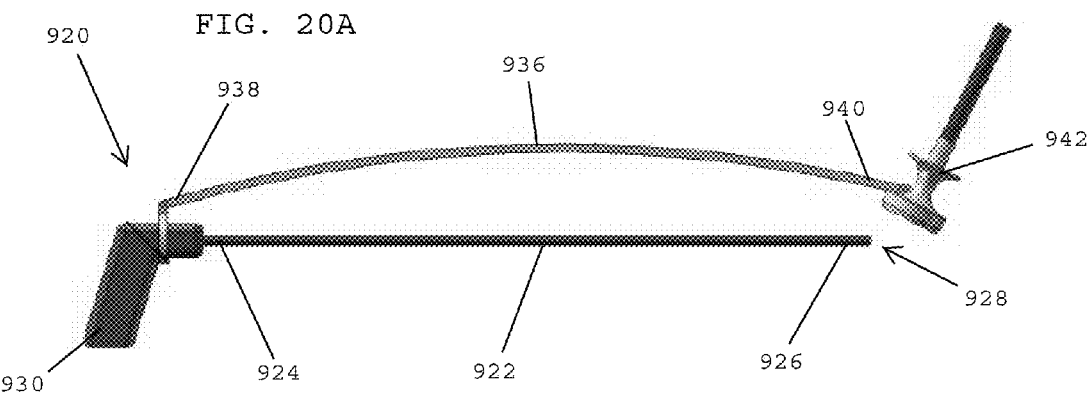
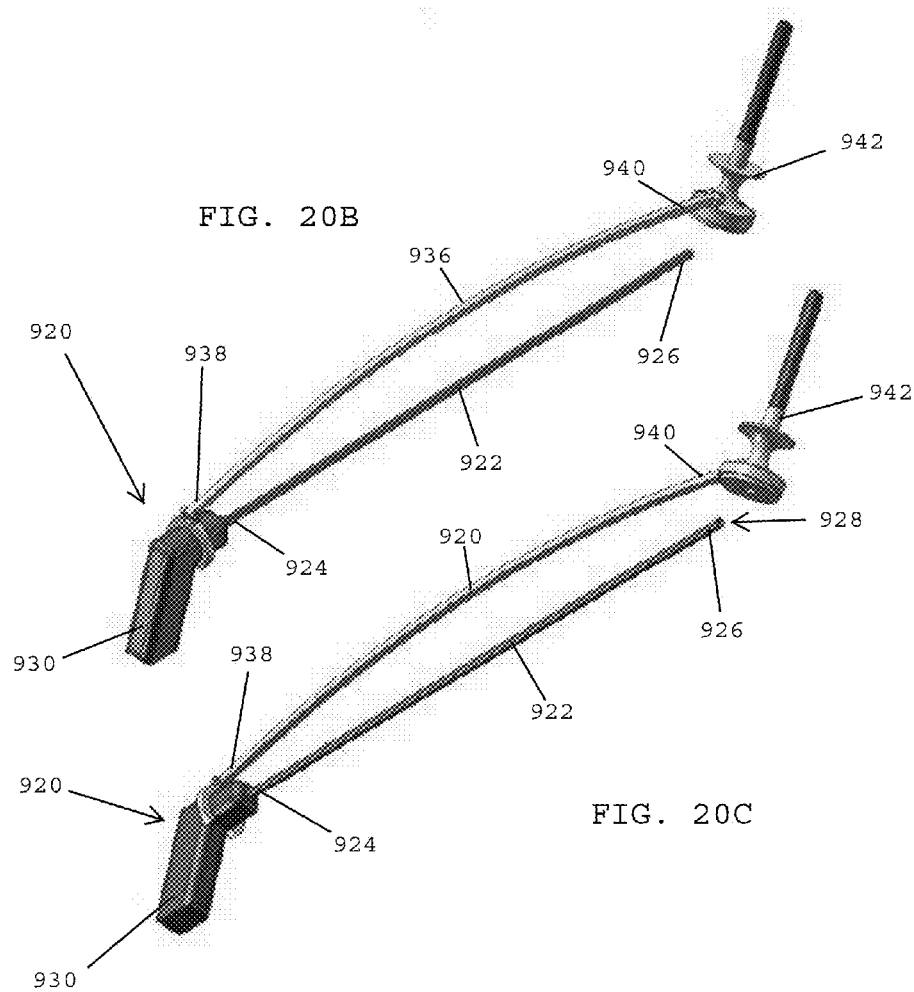

DEVICES FOR DISPENSING SURGICAL FASTENERS INTO TISSUE WHILE SIMULTANEOUSLY GENERATING EXTERNAL MARKS THAT MIRROR THE NUMBER AND LOCATION OF THE DISPENSED SURGICAL FASTENERS

CROSS REFERENCE TO RELATED APPLICATIONS

The present application is related to commonly assigned U.S. patent application Ser. No. 13/421,975, filed on even date herewith, entitled "CLAMPING DEVICES FOR DISPENSING SURGICAL FASTENERS INTO SOFT MEDIA," the disclosure of which is hereby incorporated by reference herein.

BACKGROUND OF THE INVENTION

1. Field of the Invention

The present invention relates to dispensing surgical fasteners, and more specifically relates to dispensing devices for surgical fasteners.

2. Description of the Related Art

Hernia is a condition in which a small loop of bowel or intestine protrudes through a weak place or defect within the abdominal muscle wall or groin of a patient. Hernias may result from a congenital defect, or may be caused by straining or lifting heavy objects. A hernia may leave the patient with an unsightly bulge of intestinal tissue protruding through the defect, and may cause pain, reduced lifting abilities, impaction of the bowel, or possibly other complications if the flow of blood is cut off to the protruding tissue.

Surgery may be required to repair a hernia. During a hernia repair procedure, the defect is accessed and carefully examined through an open incision or endoscopically through a trocar. In either case, careful examination is required due to the delicate network of vessels and nerves that surround the area of the defect. As such, surgeons must conduct hernia repair procedures with great skill and caution.

Repairing a hernia may involve closing the defect with sutures or fasteners. The hernia repair procedure may also involve placing a surgical prosthetic device such as a mesh patch over the open defect, and attaching the mesh patch to the abdominal wall or inguinal floor with conventional sutures or surgical fasteners. The mesh patch acts as a barrier and prevents expulsion of the bowel through the defect.

One type of common hernia is a ventral hernia. This type of hernia typically occurs in the abdominal wall and may be caused by a prior incision or puncture, or by an area of tissue weakness that is stressed. There are several repair procedures that can be employed by the surgeon, depending upon the individual characteristics of the patient and the nature of the hernia. In an Intra-peritoneal onlay mesh (IPOM) repair technique, a specific mesh is used with a flat repair layer fused to a fixation layer around the perimeter. The fixation layer has an opening to facilitate the insertion of a fixation device between the layers. During an IPOM repair, an incision is made directly over the site of the ventral hernia. The mesh is rolled and inserted through the incision and hernia into the pre-peritoneal space. The mesh is then centrally positioned underneath the hernia with the repair layer downward, facing the viscera. Stay sutures may be placed to position the mesh. Then, a fixation device is used to secure the fixation layer to the abdominal wall. Fixation of the top fixation layer will also secure the bottom repair layer as well. After the mesh is secured and is flat against the abdominal wall, the hernia defect and the skin incision may be closed using sutures.

At present, there are a variety of surgical instruments and fasteners used for attaching mesh patches to tissue. One of the earliest types of surgical instruments used is a surgical stapler, whereby a stack of staples are contained within a stapling cartridge, and are sequentially advanced within the instrument by a spring mechanism. A secondary mechanism is employed to separate the distal-most staple from the stack, to hold the remainder of the staples in the stack, and to feed the distal-most staple into the staple forming mechanism. Feeding mechanisms of this type are found in U.S. Pat. Nos. 5,470,010 and 5,582,616, to Rothfuss et al.

Another hernia mesh attachment instrument uses a helical wire fastener that resembles a small section of a spring. Multiple helical wire fasteners are stored serially within a 5 mm shaft, and are corkscrewed into tissue. A load spring is used to feed the plurality of helical fasteners distally within the shaft. A protrusion extends into the shaft to prevent the ejection of the stack of fasteners by the load spring to permit passage of a rotating fastener. Instruments and fasteners of these types are found in U.S. Pat. Nos. 5,582,616 and 5,810,882 to Bolduc et al., and U.S. Pat. No. 5,830,221 to Stein et al.

Other surgical fasteners used for hernia mesh attachment utilize either a reloadable single shot instrument or a rotary magazine that holds a small number of fasteners. These types of surgical fastening instruments are disclosed in U.S. Pat. Nos. 5,203,864 and 5,290,297 to Edward Phillips. These instruments have not gained acceptance by the surgical community, possibly due to their single shot capabilities and the large size of the rotary magazine, which can restrict use of such an instrument to an open procedure.

U.S. Pat. Nos. 5,601,573; 5,833,700; and 5,921,997 to Fogelberg et al. teach a clip applier with a feeding mechanism that utilizes a reciprocating feed bar to feed a stack of clips. A feeder shoe operably engages with and moves with the distally moving feed bar and slidingly engages with the proximally moving feed bar. The feeder shoe pushes the stack of clips distally with the distally moving feed bar and remains stationary relative to the proximally moving feed bar. A valving mechanism separates the distal-most clip from the stack holds the stack stationary as the distal-most clip may be dispensed onto a vessel.

U.S. Pat. No. 4,325,376 to Klieman et al teaches a clip applier that stores a stack of clips in a serial fashion within a clip magazine. The proximal-most clip is pushed distally by a pawl that is ratcheted distally by a reciprocating member with each actuation of the instrument. As the pawl ratchets distally, it pushes the stack of clips distally.

Commonly assigned U.S. Patent Application Publication No. 2002/0068947, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the surgical fasteners has a proximal end and a distal end. The device also has an actuator having at least two sequential positions. A first position for advancing the moving member distally and piercing tissue, and a second position for moving the moving member proximally, thereby deploying the distal end of the fastener.

The above-described instruments dispense the surgical fasteners along an axis that is parallel with the longitudinal axis of the instrument. In some instances, this dispensing angle makes it difficult for medical personnel to insert surgical fasteners along axes that are normal to the surface of the tissue receiving the fasteners. Moreover, conventional instruments require the operator to use his or her hand as a backup for providing an opposing force on the tissue receiving the fasteners. This often results in medical personnel being pricked by the sharp ends of the surgical fasteners.

In view of the above-noted deficiencies, there remains a need for improved systems, devices and methods for more economically and efficiently securing prosthetic devices using surgical fasteners. In particular, there remains a need for instruments that easily dispense surgical fasteners at angles that are perpendicular to the surface of the tissue receiving the fasteners. There also remains a need for instruments that do not require medical personnel to use a second hand as an anvil for the tissue receiving the surgical fastener. There also remains a need for an instrument that dispenses a surgical fastener when sufficient compression has been applied and that provides an indication that a predetermined compression level has been attained. There also remains a need for a device that provides a clear map on the patient's outer skin surface that indicates where the surgical fasteners have been inserted, as well as the total number of surgical fasteners that have been dispensed into tissue.

SUMMARY OF THE INVENTION

During hernia repair procedures, surgical fasteners are used for securing implants, such as mesh implants, to tissue. Medical devices, such as applicator guns, are typically used to dispense the surgical fasteners through the implant and into tissue to secure the implant over the hernia defect. When placing the surgical fasteners at the surgical site, it is critical that proper spacing exists between adjacent surgical fasteners. If the gap between adjacent fasteners exceeds 2 cm, the risk of entrapment between the abdominal wall and the implant increases dramatically. This can adversely impact tissue in-growth or cause severe complications.

During laparoscopic procedures, surgical personnel can clearly view the placement site for the surgical fasteners. As a result, it is easy for surgical personnel to properly position and space the surgical fasteners at the surgical site. Such is not the case for open IPOM procedures. Typically, in open IPOM procedures, the positioning and placement of the surgical fasteners is done blindly, using tactile feedback. Tactile feedback is required to check if enough surgical fasteners are placed for a proper fixation without gaps in between adjacent surgical fasteners. Checking where the surgical fasteners have already been placed is nearly impossible. As a result, accurate control and placement of the surgical fasteners at the surgical site is more difficult to achieve. In spite of the above-described difficulties, with open IPOM procedures, it remains absolutely critical to accurately place surgical fasteners.

In response to the above-described problems, the present invention provides a marking assembly for surgical fastener fixation devices, such as a clamp-like fixation device or an applicator gun. For clamp-like fixation devices, the marking assembly may be easily secured to a modified clamp counterpart. In applicator gun devices, the marking assembly may be coupled with an elongated dispensing tube or a handle portion of the device.

With a marker assembly directly attached to the surgical fastener fixation device, surgical personnel are able to see on the skin where the surgical fastener has been placed "internally." On the external surface of the skin, the marking assembly will generate a copy or image of where the surgical fasteners have been secured to the abdominal wall. In addition, medical personnel may check how many surgical fasteners have already been placed into the tissue.

In one embodiment, the marking assembly may be connected directly to a clamp device. In one embodiment, the marking assembly may be connected to a cannula-like device using an elongated member or arm. In one embodiment, the elongated member or arm may be solid but may also have sufficient flexibility for enabling external marking on the skin. In one embodiment, the arm is connected to the handle of the cannula-like device via a clamp. The marking assembly preferably includes structure for being grasped by the fingers or hands of the surgical personnel. In one embodiment, the marking assembly is not connected to the clamp device or the cannula-like device. In this embodiment, the marking assembly is a separate element that may be used externally for marking the exterior skin surface to indicate the number of surgical fasteners inserted into the tissue and the spacing between adjacent surgical fasteners.

In one embodiment, the marking assembly includes a pen, ink marker, pencil, or crayon. In one embodiment, the marking assembly uses a thorn or needle that pierces the outer skin surface. In this embodiment, the marking assembly includes a round cylindrical member having multiple parts. A first part is moved against a second part upon applying pressure on the external skin surface. As the first and second parts move toward each other under pressure, a thorn or needle on the second part is pushed through a central opening on the first part for piercing the skin for leaving a mark. The marking assembly including a thorn or needle may be directly connected to a clamp fixation device, or used with a cannula-like fixation device.

In one embodiment, a device is adapted for dispensing surgical fasteners inside a body while generating marks outside the body that indicate how many and where the surgical fasteners have been dispensed inside the body. The marks generated on an external surface of the body (e.g. outer skin surface) enable medical personnel to continuously monitor how many surgical fasteners have been dispensed inside the body and the exact placement and spacing between the surgical fasteners. The device preferably includes a first member having a surgical fastener dispenser opening at a distal end thereof adapted for dispensing surgical fasteners into tissue, and a second member coupled with the first member, the second member having a distal end that opposes the surgical fastener dispenser opening. The device desirably has a marking assembly secured to the distal end of the second member. In one embodiment, the marking assembly is pivotally secured to the distal end of the upper arm. In one embodiment, the marking assembly is moveable away from and toward the surgical fastener dispenser opening. The marking assembly is adapted for generating marks on an external surface that mirror the location of each surgical fastener dispensed from the surgical fastener opening at the distal end of the first member.

In one embodiment, the surgical fastener dispenser opening is adapted for insertion into a surgical opening formed in the body for dispensing the surgical fasteners into tissue inside the surgical opening with the marking assembly positioned outside the surgical opening and over an external surface of the body.

In one embodiment, the first member includes a lower arm having a distal end with the surgical fastener dispenser opening, and the second member includes an upper arm having a proximal end that is coupled with the lower arm via a pivotal connection. In one embodiment, a surgical fastener dispenser is secured to the distal end of the lower arm. The surgical fastener dispenser desirably includes the surgical fastener dispenser opening.

In one embodiment, the device has an actuator coupled with the upper and lower arms for selectively moving the arms between an open position in which the marking assembly is spaced from the surgical fastener dispenser and a closed position in which the marking assembly is closer to the surgical fastener dispenser for clamping tissue between the marking assembly and the surgical fastener dispenser.

In one embodiment, the marking assembly includes a marker adapted to contact the external surface outside the surgical opening for generating the marks on the external surface. The external marks mirror the location of the surgical fasteners dispensed into the tissue inside the surgical opening.

The marker is preferably adapted to generate a visible pattern of the marks on the external surface indicating the number and location of the surgical fasteners dispensed into the tissue inside the surgical opening. The marker may be any item used for marking a surface such as a pen, a felt marker, a pencil, a crayon, a needle, and/or a thorn.

In one embodiment, the marking assembly includes a pad connected to the distal end of the upper arm. The pad preferably has a bottom surface adapted to apply a clamping force, and an opening is formed in the bottom surface of the pad. In one embodiment, the marker is coupled with the pad and has a marking surface accessible through the opening formed in the bottom surface of the pad for marking the external surface.

In one embodiment, when the device is closed, the bottom surface of the pad desirably applies the clamping force upon the external surface which, in turn, applies a compression force through the tissue and upon the surgical fastener dispenser for dispensing one of the surgical fasteners from the surgical fastener dispenser opening and into the tissue inside the surgical opening.

In one embodiment, the device may be a cannula-like device (e.g. as applicator gun), whereby the first member is an elongated tube having the surgical fastener dispenser opening at the distal end thereof. The second member may have a proximal end coupled with the first member and a distal end that opposes the surgical fastener dispenser opening.

In one embodiment, the device may include a handle connected with a proximal end of the elongated tube, whereby the second member is secured to the handle. In one embodiment, the second member is preferably flexible for moving the distal end of the second member toward and away from the surgical fastener dispenser opening at the distal end of the elongated tube.

In one embodiment, a device is adapted for dispensing surgical fasteners into tissue inside a surgical opening while simultaneously generating marks on an external surface outside the surgical opening. The device desirably includes a lower arm having a proximal end and a distal end including a surgical fastener dispenser opening adapted for dispensing surgical fasteners, and an upper arm coupled with the lower arm and having a distal end that opposes the surgical fastener dispenser opening at the distal end of the lower arm. A marking assembly is desirably secured to the distal end of the upper arm and opposes the surgical fastener dispenser opening at the distal end of the lower arm. In one embodiment, the distal ends of the upper and lower arms are moveable between an open position and a closed position. In one embodiment, when the upper and lower arms are in the closed position the marking device is adapted to generate a mark on the external surface outside the surgical opening each time a surgical fastener is dispensed into tissue within the surgical opening. Each of the marks desirably mirrors the location of one of the surgical fasteners dispensed inside the surgical opening.

In one embodiment, the marker is adapted to contact the external surface each time one of the surgical fasteners is dispensed into the tissue inside the surgical opening for providing a visible pattern of markings on the external surface indicating the number and location of each the surgical fastener dispensed into the tissue inside the surgical opening.

In one embodiment, the device may include an actuator coupled with the upper and lower arms for selectively moving the upper and lower between an open position in which the marking assembly is spaced from the surgical fastener dispenser and a closed position in which tissue is clamped between the marking assembly and the surgical fastener dispenser. In one embodiment, the actuator desirably has a hand grip secured to the lower arm, and a trigger mounted on the lower arm and linked with the upper arm, whereby the trigger is adapted for being pulled toward the hand grip for moving the arms into the closed position, and the trigger is adapted for moving away from the hand grip for moving the arms into the open position. The device desirably has a trigger return spring coupled with the trigger for normally urging the trigger to move away from the hand grip.

In one embodiment, a clamping device dispenses surgical fasteners into internal tissue inside a surgical opening while simultaneously generating external marks on an external surface outside the surgical opening. The markings on the external surface desirably mirror the location of each dispensed surgical fastener. In one embodiment, the clamping device desirably includes a first arm including a surgical fastener dispenser, a second arm opposing the first arm, and a marking assembly secured to the second arm for generating the external marks on the external surface. In one embodiment, the surgical fastener dispenser is secured to a distal end of the first arm, and the marking assembly is secured to a distal end of the second arm. The surgical fastener dispenser preferably has a surgical fastener dispenser opening through which the surgical fasteners are dispensed into the internal tissue inside the surgical opening.

In one embodiment, the device preferably includes an actuator coupled with the first and second arms for selectively moving the first and second arms between an open position in which the marking assembly is spaced from the surgical fastener dispenser and a closed position in which the tissue is compressed between the marking assembly and the surgical fastener dispenser. In one embodiment, as the tissue is compressed between the distal ends of the arms at the working end of the device, a surgical fastener is dispensed into tissue inside the surgical opening and the marking assembly makes an external mark on an external skin surface that indicates the exact location of the dispensed surgical fastener. The clamping device is designed to make an external mark each time one of the surgical fasteners is dispensed so that medical personnel may track the total number of surgical fasteners that have been dispensed and the exact location of each dispensed surgical fastener.

In one embodiment, a clamping device is adapted for dispensing surgical fasteners into tissue inside a surgical opening while simultaneously generating external marks on an external surface outside the surgical opening that mirror the location of each dispensed surgical fastener. The clamping device desirably includes a lower arm having a proximal end, a distal end, and a longitudinal axis extending between the proximal and distal ends, and a surgical fastener dispenser secured to the distal end of the lower arm, the surgical fastener dispenser including a surgical fastener dispenser opening. In one embodiment, the clamping device desirably includes an upper arm coupled with the lower arm and having a distal end that opposes the distal end of the lower arm, and a marking assembly connected to the distal end of the upper arm and opposing the surgical fastener dispenser.

In one embodiment of the present invention, a clamping device includes a surgical fastener dispenser adapted to dispense surgical fasteners into soft media for securing prosthetic devices, such as surgical mesh implants, to the soft media. Specifically, the embodiment may be used for the fixation of layered mesh implants during an IPOM repair. The clamping device preferably includes a pair of opposing arms that are adapted for being positioned on opposing sides of the target soft media. A first one of the arms may be positioned inside a surgical opening for opposing an inner surface of the soft media (e.g. the peritoneum of the inner abdominal wall) and the second one of the arms may be positioned outside the surgical cavity for opposing an outer surface of the soft media (e.g. a patient's outer skin surface).

In one embodiment, the clamping device preferably includes a fixed lower arm having a pistol grip handle, and a sliding trigger coupled with an actuation assembly used for closing the distal ends of the upper and lower arms and for generating a clamping force on opposite surfaces of the target media. During a clamping operation, the clamping device desirably performs three functions, namely, clamping the soft media, delivering surgical fasteners one at a time into the soft media at an angle that is normal to the surface of the soft media for securing a prosthetic device to the soft media, and preparing the clamping device for dispensing another surgical fastener during the next firing cycle. In one embodiment, the clamping device may deliver surgical fasteners into the soft media at an angle that is not normal or perpendicular to the surface of the soft media.

In one embodiment, the surgical fastener dispenser preferably includes a sterile cartridge body that contains a predetermined number of surgical fasteners (e.g. 20), pre-loaded in the cartridge body for providing the clamping device with multi-fire capabilities. In one embodiment, the cartridge body may be sterilized as a separate component before being loaded onto the lower arm, such as the distal end of the lower arm.

The clamping device disclosed herein desirably dispenses surgical fasteners in a consistent, controlled and repeatable manner from the distal end of the clamping device. It is preferred that all of the surgical fasteners be inserted into soft media with the same force and at the same angle. In one embodiment, the distal end of the surgical fastener dispenser preferably has a spacer or alignment element that is first positioned against the seam or edge of a mesh patch (e.g. the seam of a layered mesh pocket) for insuring that surgical fastener dispensed from the surgical fastener dispenser is delivered at a location that is a fixed distance away from the seam. The spacer enables surgical personnel to reliably and repeatedly deliver the surgical fasteners at the fixed distance away from the seam.

In one embodiment, during initial insertion and positioning of the surgical fastener dispenser within a surgical opening, the spacer at the distal end of the cartridge body preferably conceals the surgical fasteners and an insertion fork used for inserting the surgical fasteners. The surgical fasteners and the insertion fork are preferably exposed only after the lower arm and the surgical fastener dispenser has been properly inserted and positioned. In one embodiment, the cartridge body is pivotally connected with a support tray of the surgical fastener dispenser, and the distal end of the cartridge body deflects or pivots downwardly during compression of the clamping device for exposing a surgical fastener loaded onto the insertion fork.

In one embodiment, a force limiting system prevents a user from exerting excess compression forces and undue stress upon the surrounding tissue. In one embodiment, the clamping device preferably includes a pre-loaded extension spring connecting two ends of one of the clamping arms. In one embodiment, the extension spring is desirably attached at an angle, thereby creating torque between the two components. The spring allows the clamping device to close until the torque value is reached. At that point, the compression force exceeds the pre-load level on the extension spring and the spring begins to take up any remaining compression forces, thereby preventing further travel of the distal end of the arm while enabling the proximal end of the arm to continue traveling.

In one embodiment, the jaws of the clamping device provide a sizeable opening and may includes adjustable features that compensate for a range of patient tissue thicknesses and mesh having different sizes, shapes and dimensions. Moreover, the clamping device disclosed herein may be used with rolled flat meshes and layered, skirted meshes.

In one embodiment, the clamping device preferably includes a pad secured to a distal end of one of the arms. The pad self-adjusts to provide an opposing force for the surgical fastener dispenser. The self-adjusting pad also facilitates one-handed use because there is no need to provide counter pressure with a user's second hand. In one embodiment, the pad is a pivoting pad secured to the distal end of one of the arms. In one embodiment, the pad is secured to one of the arms using a linear mechanism.

In one embodiment, the clamping device has a slide grip handle that preferably provides for secure control and allows for one-handed use. The slide grip handle also preferably allows the user's hand to be free of obstructions and provides a clear line of sight for inserting the distal end of the device into a cavity. In one embodiment, the clamping device is preferably actuated by transferring linear force on the trigger through a rack and pinion system to generate rotary torque.

In one embodiment, the clamping device may include a pivot style handle that is offset from the arms for ergonomic single-handed use. The arms preferably pivot around a main pivot point, which results in torque being delivered to the clamping ends of the arms.

In one embodiment, the pivoting pad desirably includes a marker that enables a surgeon to determine and see on the skin where the surgical fasteners have been positioned internally. Because the marker aligns with the dispenser opening when a surgical fastener is dispensed, the marker produces an exact copy or image of the location of the surgical fastener that has been inserted into the abdominal wall. In addition, the marker system also preferably provides an indication of the total number of surgical fasteners that have been dispensed into the abdominal wall.

In one embodiment, a clamping device for dispensing surgical fasteners preferably includes a lower arm having a proximal end, a distal end, and a longitudinal axis extending between the proximal and distal ends, and an upper arm pivotally connected with the lower arm and having a distal end that opposes the distal end of the lower arm. The upper arm is preferably curved and has a concave surface that opposes the lower arm. The clamping device desirably includes an actuator coupled with the upper and lower arms for moving the distal ends of the upper and lower arms toward one another for closing the clamping device.

In one embodiment, a surgical fastener dispenser is preferably secured to the distal end of the lower arm for dispensing surgical fasteners. The surgical fastener dispenser desirably includes a cartridge body having a top surface with a surgical fastener dispenser opening formed therein. A plurality of surgical fasteners is desirably pre-loaded into the cartridge body for being dispensed one at a time through the dispenser opening. The clamping device preferably includes a pad pivotally connected to the distal end of the upper arm, the pad having a bottom surface that opposes the dispenser opening. In one embodiment, when the clamping device is closed, the pad pivots for self-adjusting so that the bottom surface of the pad applies a clamping force upon the top surface of the cartridge body for dispensing one of the surgical fasteners from the dispenser opening.

In one embodiment, the actuator preferably includes a hand grip secured to the lower arm, and a trigger mounted on the lower arm and linked with the upper arm. The trigger is adapted for being pulled toward the hand grip for closing the clamping device for generating a clamping force and dispensing a surgical fastener. The trigger is adapted for moving away from the hand grip for opening the clamping device to release the clamping force. In one embodiment, the actuator desirably includes a trigger return spring coupled with the trigger for normally urging the trigger to move away from the hand grip.

The actuator may also include a rack and pinion system linking the trigger with the upper arm. In one embodiment, the rack and pinion system desirably includes a rack having teeth. The rack slides along the longitudinal axis of the lower arm. The proximal end of the upper arm includes a pinion having teeth that mesh with the teeth on the rack.

In one embodiment, the surgical fastener dispenser preferably includes a support tray having a proximal end connected with the distal end of the lower arm, and a distal end including an insertion fork that extends along an axis that is perpendicular to the longitudinal axis of the lower arm, whereby the cartridge body overlies the support tray. In one embodiment, the cartridge body preferably has a proximal end pivotally connected with the proximal end of the support tray, and a distal end freely moveable relative to the distal end of the support tray, the top surface of the cartridge body extending between the proximal and distal ends of the cartridge body and the dispenser opening being in alignment with the insertion fork. The surgical fastener dispenser also preferably includes a cartridge body return spring in contact with the cartridge body and the support tray for normally urging the distal end of the cartridge body away from the support tray, whereby the surgical fasteners are arrayed in a series for being dispensed one at a time from the dispenser opening, and whereby each of the surgical fasteners has an insertion end oriented toward the top surface of the cartridge body. In one embodiment, the cartridge body return spring preferably engages the cartridge body and the support tray for normally urging the top surface of the cartridge body into a plane that is parallel with the longitudinal axis of the lower arm. In one embodiment, the cartridge body is not pivotally connected to the support tray and the cartridge body is adapted to move up and down relative to the support tray.

In one embodiment, the surgical fastener dispenser may include a surgical fastener advancer spring in communication with the surgical fasteners for urging the surgical fasteners toward the distal end of the cartridge body. The surgical fastener advancer spring is preferably adapted to urge a leading surgical fastener to move into engagement with the insertion fork at the distal end of the support tray for being dispensed through the dispenser opening of the cartridge body.

The surgical fasteners preferably extend along planes that are parallel with one another and perpendicular to the longitudinal axis of the lower arm. In one embodiment, the insertion fork is desirably adapted to hold and dispense the surgical fasteners along an axis that is perpendicular to the longitudinal axis of the lower arm.

In one embodiment, the cartridge body is preferably pivotable between an extended position in which the top surface of the cartridge body is parallel with the longitudinal axis of the lower arm and a depressed position in which the top surface of the cartridge body is angled relative to the longitudinal axis of the lower arm. In one embodiment, the cartridge body is under compression by the pad when in the depressed position. The cartridge body return spring is preferably compressed when the cartridge body is in the depressed position.

In one embodiment, the leading surgical fastener in the series of surgical fasteners and the insertion fork are covered by the cartridge body when the cartridge body is in the extended position. When the cartridge body is in the depressed position, the leading surgical fastener and the insertion fork are at least partially exposed through the dispenser opening for inserting the surgical fastener into soft media.

In one embodiment, the cartridge body preferably has a spacer projecting from a distal end thereof that extends beyond the distal end of the support tray for spacing the dispenser opening from a distal-most end of the surgical fastener dispenser. The spacer facilitates aligning the surgical fastener dispenser relative to an edge or seam of a surgical mesh to insure that the surgical fasteners are inserted an appropriate distance away from the edge or seam.

In one embodiment, the pad on the upper arm desirably includes a marker accessible at the bottom surface thereof that is aligned with the dispenser opening when the clamping device is closed. The marker is desirably adapted to produce a visual indicator on a patient's outer skin surface that mirrors the location of one of the surgical fasteners inserted into the patient's inner surface.

In one embodiment, the pad desirably includes a beveled washer adapted to generate an audible clicking sound when the clamping force between the pad and the cartridge body reaches a predetermined level. The clicking sound provides an indication that sufficient compression force has been applied to the soft media for dispensing one of the surgical fasteners into the soft media.

In one embodiment, a clamping device for dispensing surgical fasteners preferably includes a lower arm having a proximal end, a distal end, and a longitudinal axis extending between the proximal and distal ends, and an upper arm pivotally connected with the lower arm and having a distal end that opposes the distal end of the lower arm. The clamping device desirably has an actuator coupled with the upper and lower arms for moving the distal ends of the upper and lower arms toward one another for closing the clamping device for generating a clamping force therebetween.

A surgical fastener dispenser may be secured to the distal end of the lower arm. The surgical fastener dispenser desirably has a plurality of surgical fasteners loaded therein. The surgical fastener dispenser preferably includes a dispenser opening adapted to dispense the surgical fasteners one at a time.

The clamping device desirably includes a pad pivotally connected to the distal end of the upper arm, the pad having a bottom surface that opposes the dispenser opening, whereby when the clamping device is closed, the bottom surface of the pad applies an opposing clamping force upon the top surface of the surgical fastener dispenser for dispensing one of the surgical fasteners along an axis that is perpendicular to the longitudinal axis of the lower arm.

In one embodiment, the surgical fastener dispenser desirably includes a support tray having a proximal end connected with the distal end of the lower arm, and a distal end including an insertion fork that extends along an axis that is perpendicular to the longitudinal axis of the lower arm. The dispenser preferably includes a cartridge body overlying the support tray, the cartridge body having a proximal end pivotally connected with the proximal end of the support tray, a distal end freely moveable relative to the distal end of the support tray, a top surface extending between the proximal and distal ends of the cartridge body, and the surgical fastener dispenser opening formed in the top surface and being in alignment with the insertion fork. The surgical fastener dispenser also desirably includes a cartridge body return spring in contact with the cartridge body and the support tray for normally urging the distal end of the cartridge body away from the support tray.

In one embodiment, a plurality of surgical fasteners may be disposed within the cartridge body, with the surgical fasteners arrayed in a series for being dispensed one at a time from the dispenser opening. Each of the surgical fasteners preferably has an insertion end oriented toward the top surface of the cartridge body. In one embodiment, when the clamping device is closed, the bottom surface of the pad applies a clamping force upon the top surface of the cartridge body. The cartridge body is pivotable between an extended position in which the top surface of the cartridge body is parallel with the longitudinal axis of the lower arm and a depressed position in which the top surface of the cartridge body is angled relative to the longitudinal axis of the lower arm.

These and other preferred embodiments of the present invention will be described in more detail below.

BRIEF DESCRIPTION OF THE DRAWING

FIG. 5 shows an insertion fork of the surgical fastener dispenser of FIGS. 3A-3B aligned with the surgical fastener shown in FIGS. 4A-4C.

FIGS. 19A-19C show a device for dispensing surgical fasteners having a marking assembly coupled therewith, in accordance with one embodiment of the present invention.

FIGS. 20A-20C show a device for dispensing surgical fasteners having a marking assembly coupled therewith, in accordance with another embodiment of the present invention.

DETAILED DESCRIPTION

Figure 1:
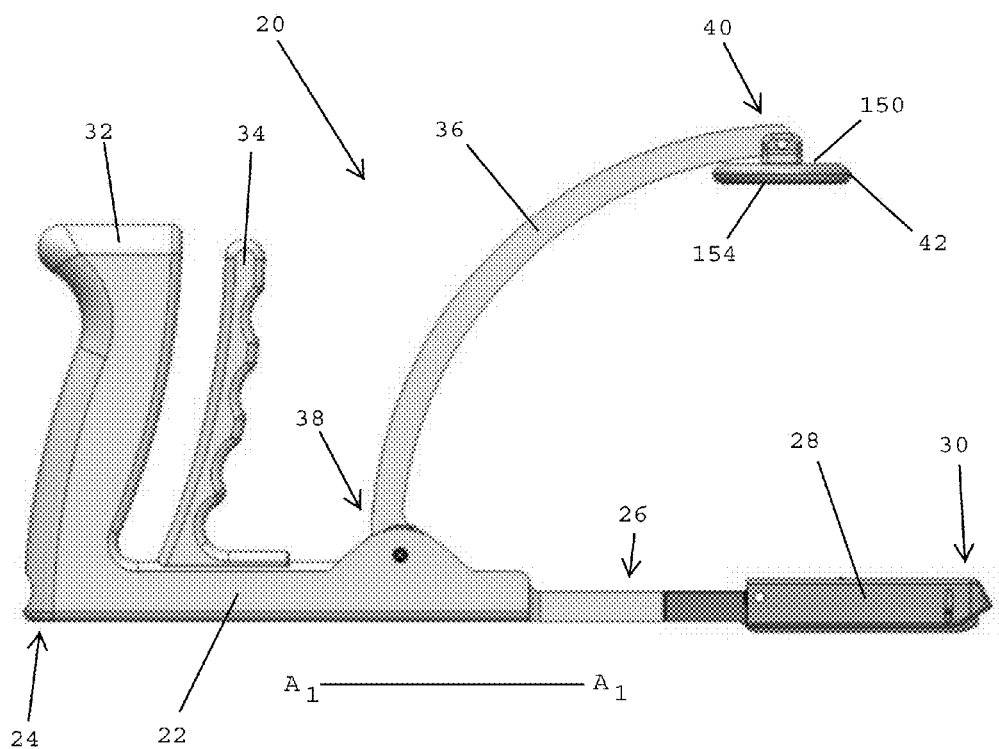
FIG. 1 shows a right side view of a clamping device for dispensing surgical fasteners including a lower arm, a surgical fastener dispenser secured to a distal end of the lower arm, and an upper arm that opposes the surgical fastener dispenser for producing a clamping force, in accordance with one embodiment of the present invention.

Referring to FIG. 1, in one embodiment, a clamping device 20 for dispensing surgical fasteners into soft media preferably includes a lower arm 22 having a proximal end 24 and a distal end 26, and a surgical fastener dispenser 28 secured to the distal end 26 of the lower arm 22. The surgical fastener dispenser has a distal end 30 that is adapted to dispense a single surgical fastener during each firing cycle, as will be described in more detail herein. The lower arm 22 desirably extends along a longitudinal axis $A_1$-$A_1$. The clamping device 20 preferably includes a handle 32 provided at the proximal end 24 of the lower arm 22 and a trigger 34 that is adapted to slide relative to the lower arm, preferably along the longitudinal axis A1-A1, for operating the clamping device. The handle 32 preferably has a forward leaning angle toward the distal end 26 of the lower arm 22, which ensures that the user's hand and wrist may be in a more favorable ergonomic position during operation of the clamping device 20.

In one embodiment, the clamping device 20 preferably includes an upper arm 36 having a proximal end 38 and a distal end 40. The proximal end 38 of the upper arm 36 is pivotally secured to the lower arm 22, preferably via a rack and pinion system. In one embodiment, the upper arm 36 defines an arc or curve. The clamping device 20 desirably includes a pad 42 pivotally connected to the distal end 40 of the upper arm 36. The pad 42 preferably pivots so that the pad may self-adjust for opposing the top surface of the surgical fastener dispenser 28 when the distal end 40 of the upper arm 36 is pivoted toward the cartridge assembly 28 for being moved into a closed, clamping position.

Figure 2:
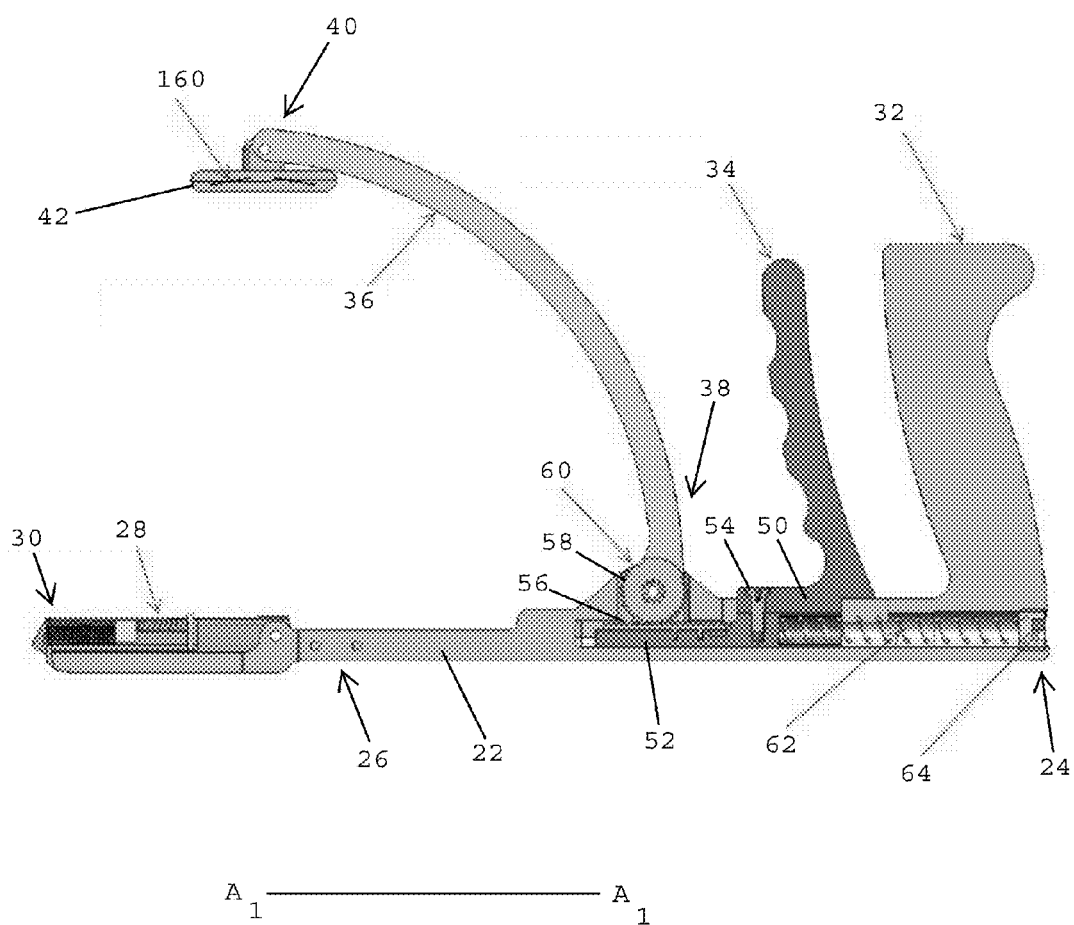
FIG. 2 shows a cross-sectional view of a left side of the clamping device shown in FIG. 1.

Referring to FIG. 2, in one embodiment, the lower arm 22 preferably includes the handle 32 and the slideable trigger 34 coupled therewith. The slideable trigger 34 desirably includes a lower end 50 that is secured to a rack 52 of a rack and pinion system via a fastener 54. The rack 52 preferably includes rack teeth 56 that engage pinion teeth 58 on a pinion 60, which is preferably secured to the proximal end 38 of upper arm 36. The clamping device 20 desirably includes a trigger return spring 62 extending between a proximal end of the rack 52 and a spring tensioner 64 insertable into an opening at a proximal end 24 of the lower arm 22.

In operation, as the trigger 34 is pulled toward the proximal end 24 of the lower arm 22, the trigger 34 and the rack 52 move along the axis $A_1$-$A_1$, toward the proximal end 24 of the lower arm 22. The rack 52 rotates the pinion 60 in a counter-clockwise direction, which swings the distal end 40 of the upper arm 36 and the pad 42 toward the distal end 30 of the surgical fastener dispenser 28. As the distal end 40 of the upper arm 36 moves toward the cartridge assembly 28, the pad 42 preferably moves into opposing alignment with the distal end 30 of the surgical fastener dispenser 28. As the trigger 34 moves toward the handle 32, the trigger return spring 62 is preferably compressed between the rack 52 and the spring tensioner 64. When the trigger 34 is released, the energy stored in the trigger return spring 62 urges the trigger 34 to slide along the axis $A_1$-$A_1$ toward the distal end 26 of the lower arm 22.

Figure 3A:
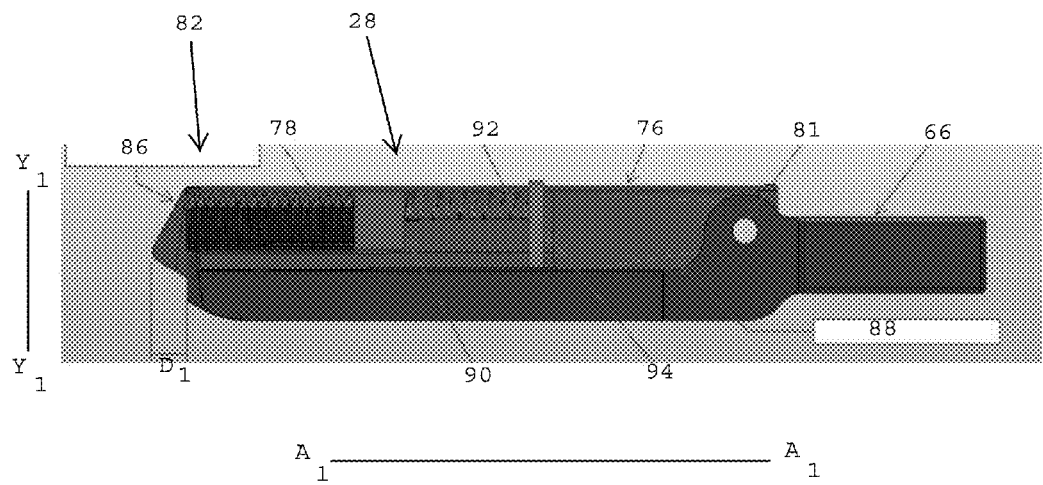
FIG. 3A shows a left side view of the surgical fastener dispenser shown in FIGS. 1 and 2.
Figure 3B:
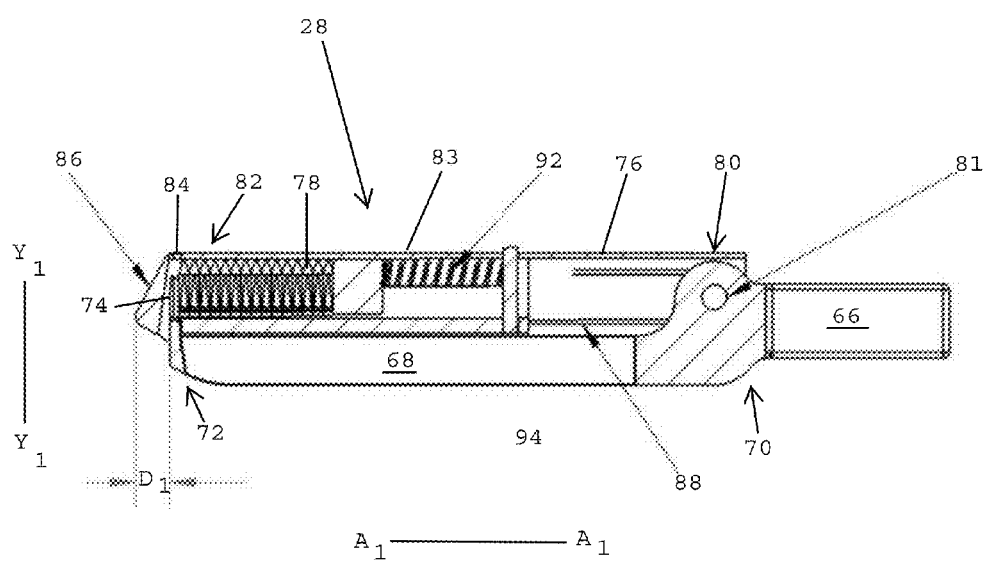
FIG. 3B shows a cross-sectional view of the surgical fastener dispenser shown in FIG. 3A.

Referring to FIGS. 3A and 3B, in one embodiment, the surgical fastener dispenser 28 preferably includes an attachment arm 66 that is securable to the distal end 26 of the lower arm 22 of the clamping device 20 (FIG. 2). The surgical fastener dispenser 28 desirably has a support tray 68 that projects distally from the attachment arm 66. The support tray 68 preferably has a proximal end 70 adjacent the attachment arm 66, a distal end 72 spaced from the proximal end 70, and an insertion fork 74 that projects upwardly from the distal end 72 of the support tray 68. In one embodiment, the attachment arm 66 and the support tray 68 preferably extend along the longitudinal axis $A_1$-$A_1$ of the lower arm 22 (FIG. 2), and the fork 74 preferably extends along a vertical axis $Y_1$-$Y_1$ that is perpendicular to the axis $A_1$-$A_1$. As will be described in more detail herein, the insertion fork 74 is adapted to engage a surgical fastener for driving the surgical fastener into soft media, such as tissue.

In one embodiment, the surgical fastener dispenser 28 desirably includes a cartridge body 76 having a plurality of surgical fasteners 78 loaded therein. The cartridge body 76 preferably has a proximal end 80 that is pivotally secured to the proximal end 70 of the support tray 68 via pivot pin 81, and a distal end 82 that is free to pivot toward and away from the distal end 72 of the support tray 68. The cartridge body 76 preferably has a dispenser opening 84 adjacent the distal end 82 thereof through which the fork 74 and surgical fasteners 78 may pass. In one embodiment, as the distal end 82 of the cartridge body 76 moves downwardly toward the distal end 72 of the support tray 68, the insertion fork 74 and a lead surgical fastener loaded on the insertion fork pass through the dispenser opening 84 in the cartridge body 76. The distal end 82 of the cartridge body 78 desirably includes a spacer 86 that projects a distance $D_1$ beyond the distal end 72 of the support tray 68. As will be described in more detail herein, the spacer 86 preferably insures that the dispenser opening 84 in the cartridge body 78 is positioned inside a peripheral edge or seam of a prosthetic device, such as the peripheral edge or seam of a surgical mesh, so that a surgical fastener is not secured over the edge or seam of the prosthetic device.

In open IPOM procedures, the placement of surgical fasteners or tacks used for fixation is absolutely critical. The surgical fasteners should be placed a correct distance from the edge of the mesh. If an excessive gap (>5 mm) occurs, the risk of entrapment of tissue between the abdominal wall and the prosthetic mesh will increase. This may have an impact on in-growth behavior and possibly lead to severe complications. In open IPOM procedures, it is difficult to control the correct positioning of the surgical fasteners since the visual control is much more difficult in comparison to laparoscopic procedures in which surgical personnel have a clear view and control of the medical devices. The present invention provides a clamping device that overcomes the deficiencies found in prior art devices.

In one embodiment, the surgical fastener dispenser 28 preferably includes a cartridge body return spring 88 that extends between the support tray 68 and the cartridge body 76 for normally urging the cartridge body 76 to move into the initial, extended position shown in FIGS. 3A and 3B. When a downward force (generally along the axis $Y_1$-$Y_1$) is applied to the top surface 83 of the cartridge body 76, the cartridge return spring 88 is compressed between the cartridge body 76 and the support tray 68. When the force is removed, the cartridge return spring 88 urges the cartridge body 76 to pivot back into the initial position shown in FIGS. 3A and 3B, whereby the top surface 83 of the cartridge body is parallel with the axis $A_1$-$A_1$.

In one embodiment, the surgical fastener dispenser 28 preferably includes a surgical fastener advancer 90 that is adapted to urge the surgical fasteners 78 toward the distal end 82 of the cartridge body 76 for being engaged by the insertion fork 74. The surgical fastener dispenser 30 also desirably includes a surgical fastener advancer spring 92 that extends between the advancer 90 and a spring stop 94.

In one embodiment, surgical fasteners 78 are loaded in series into the cartridge body 76 of the surgical fastener dispenser 28. The surgical fastener reload spring 92 desirably urges the series of surgical fasteners 78 toward the distal end 82 of the cartridge body 28. After the insertion fork 74 has dispensed a lead surgical fastener into soft media, the next surgical fastener is advanced distally toward the distal end 82 of the cartridge body 76 for being aligned with the insertion fork 74 so that another clamping and dispensing cycle may commence. The dispensing process may be repeated until all of the surgical fasteners 78 in the cartridge body 76 have been dispensed from the surgical fastener dispenser 28. A single fastener is dispensed each time the device is clamped onto soft media.

Referring to FIGS. 4A-4D, in one embodiment, the clamp device preferably dispenses surgical fasteners 78 adapted for insertion into soft media such as tissue. The surgical fasteners 78 are preferably designed for securing a surgical mesh to tissue. The surgical fasteners and the clamping device for inserting the surgical fasteners may incorporate one or more of the features disclosed in commonly assigned U.S. patent application Ser. No. 12/464,143, filed May 12, 2009, U.S. patent application Ser. No. 12/464,151, filed May 12, 2009, U.S. patent application Ser. No. 12/464,165, filed May 12, 2009, and U.S. patent application Ser. No. 12/464,177, filed May 12, 2009, the disclosures of which are hereby incorporated by reference herein.

In one embodiment, the surgical fastener 78 desirably includes a distal end 100 and a proximal end 102, a first leg 104 having a first tip 106 provided at a distal end of the first leg, and a second leg 108 having a second tip 110 provided at a distal end of the second leg. In one embodiment, the cross-sectional dimensions of the first and second legs 104, 108 diminish when moving from the proximal ends toward the distal ends of the legs. The surgical fastener 78 preferably includes a bridge 112 adjacent the proximal end 102 of the surgical fastener that connects the proximal ends of the first and second legs 104, 108. In one embodiment, the bridge may be positioned anywhere between the proximal and distal ends of the surgical fastener as long as it interconnects the first and second legs. The surgical fastener 78 preferably includes at least one first barb 114 projecting rearwardly from the first tip 106 and at least one second barb 116 projecting rearwardly from the second tip 110. Although only one barb is shown on each leg, other surgical fasteners may have multiple barbs on each leg or tip. In one embodiment, the first and second tips 106, 110 may be conical in shape. The tips may be formed with sharp leading points or may be more obtuse.

In one embodiment, the first and second tips 106, 110 have distal piercing tips that are skewed with respect to the longitudinal axes of the respective first and second legs 104, 108. In one embodiment, the distal piercing tips are skewed outwardly with respect to the longitudinal axes of the first and second legs. The distance between the tips is preferably greater than the distance between the legs for increasing the likelihood of capturing the fibers of a prosthetic device being the legs. In one embodiment, the first and second tips 106, 110 have blunt distal piercing points, which enable the surgical fastener to penetrate tissue while minimizing unwanted penetration into the hand of an operator.

Figure 4A:
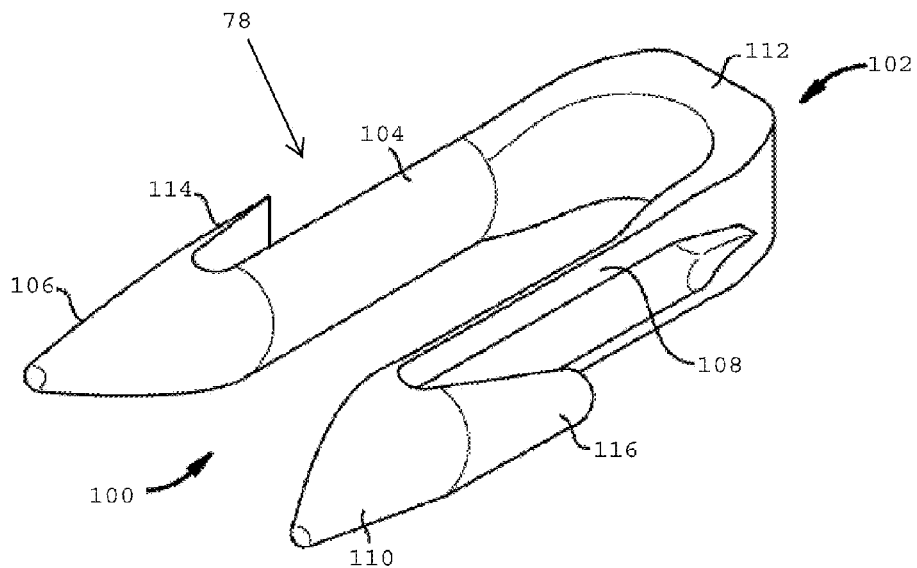
FIG. 4A shows a perspective view of a surgical fastener loaded into the surgical fastener dispenser of FIGS. 3A and 3B, in accordance with one embodiment of the present invention.
Figure 4B:
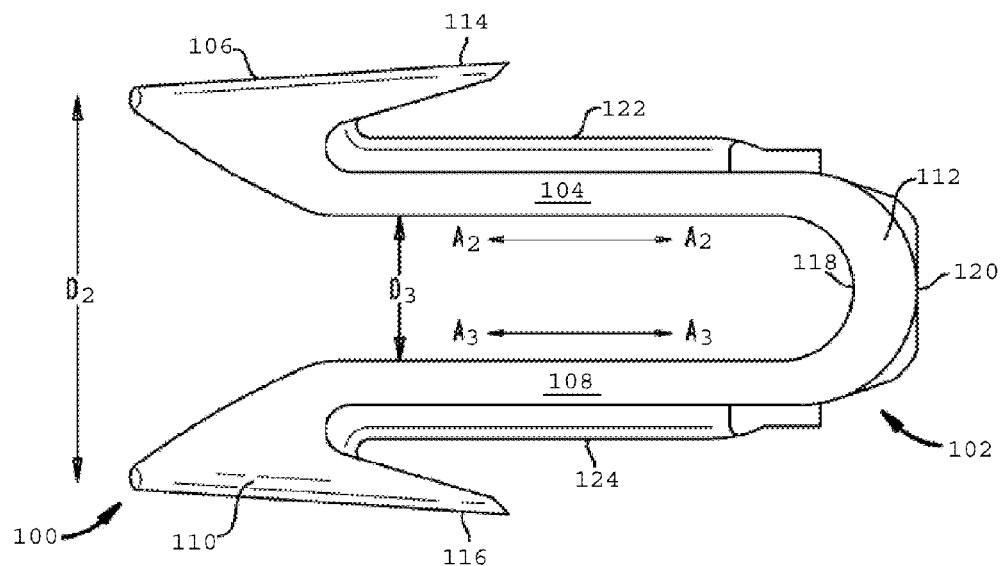
FIG. 4B shows a top plan view of the surgical fastener shown in FIG. 4A.

Referring to FIG. 4B, in one embodiment, the bridge 112 preferably includes a concave inner surface 118 facing toward the distal end 100 of the surgical fastener 78 and a convex outer surface 120 facing toward the proximal end 102 of the surgical fastener. The first leg 104 has an outer wall having a first rib 122 that extends along a longitudinal axis $A_2$-$A_2$ of the first leg, and the second leg 108 includes an outer wall having a second rib 124 that extends along the longitudinal axis $A_3$-$A_3$ of the second leg 108. In one embodiment, the distance $D_2$ between the piercing points at the distal ends of the first and second tips 106, 110 is preferably greater than the distance $D_3$ between the opposing inner surfaces of the first and second legs 104, 108. The wider relative distance between the distal piercing points of the first and second tips 106, 110 preferably ensures that the surgical fastener 78 will engage strands on a porous prosthetic device, such as the strands of a surgical mesh used for performing a hernia procedure. In one embodiment, the outwardly skewed distal piercing tips provides increased capacity to capture surgical mesh fibers where the mesh fibers are separated from one another without the need to increase the span between each leg.

Figure 4C:
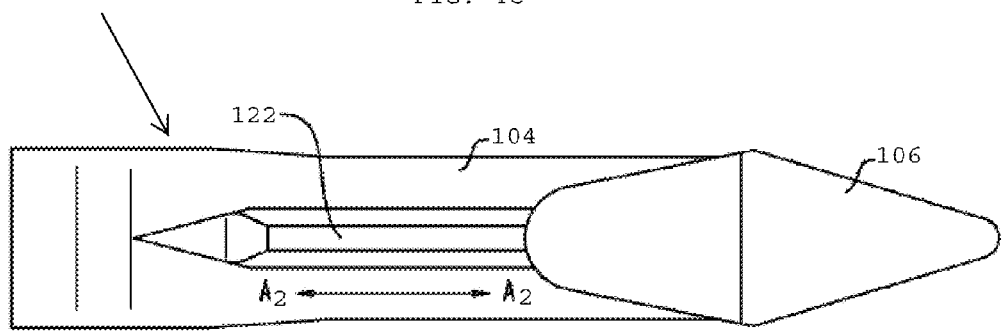
FIG. 4C shows a right side elevation view of the surgical fastener shown in FIG. 4A.
Figure 4D:
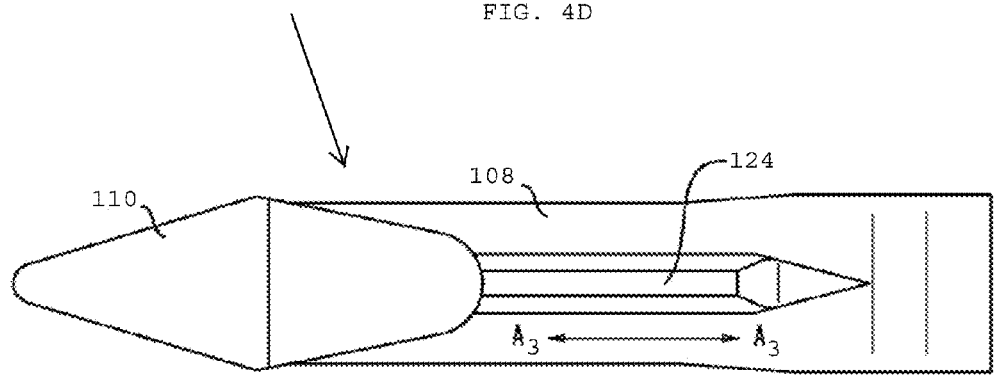
FIG. 4D shows a left side elevation view of the surgical fastener shown in FIG. 4A.

Referring to FIG. 4C, in one embodiment, the first leg 104 has the first rib 122 extending along the longitudinal $A_2$ of the first leg. When viewed from the side as shown in FIG. 4C, the first rib 122 is preferably in substantial alignment with a distal point of the first piercing tip 106. Referring to FIG. 4D, in one embodiment, the second leg 108 has a second rib 124 extending along the longitudinal axis $A_3$ of the second leg 108. When viewed from the side as shown in FIG. 4D, the second rib 124 is preferably aligned with a distal point of the second tip 110.

Referring to FIG. 5, in one embodiment, the surgical fastener 78 is preferably advanced into alignment with the insertion fork 76 located at the distal end 72 of the support tray 68 (FIGS. 3A and 3B). In one embodiment, the insertion fork 76 preferably includes an upper end 130 adapted to engage one or more surfaces of the surgical fastener 78 for guiding insertion of the surgical fastener into soft media. In one embodiment, the upper end 130 of the insertion fork 76 includes a first tine 132 having a first inner lip 134 formed therein, and a second tine 136 having a second inner lip 138 formed therein. In one embodiment, the inner lips 134, 138 preferably oppose one another and extend along the axis $Y_1$-$Y_1$ that is perpendicular with the longitudinal axis $A_1$-$A_1$ of the lower arm 22 of the clamping device 20 (FIGS. 1 and 2). In operation, the opposing inner lips 134, 138 of the first and second tines 132, 136 are preferably adapted to engage the ribs on the respective first and second legs 104, 108 of the surgical fastener 78. The engagement of the inner lips 134, 138 with the ribs preferably aligns the surgical fastener 86 with the distal end 130 of the fork 76, and stabilizes the surgical fastener during implantation into tissue. The surgical fastener 78 is brought into contact with the inner lips 134, 138 by the surgical fastener advancer spring 92. Surgical fasteners 78 are loaded along axis $A_1$-$A_1$ until they contact the lips 134, 138. The 90° angle between the insertion fork and the axis $A_1$-$A_1$, ensures that the surgical fasteners are inserted into the soft media at an angle that is normal to the surface of the soft media. In one embodiment, the distal-most tips of the first and second tines 132, 136 are advanced until they abut against convex seating surfaces provided near the distal ends of the first and second legs 104, 108.

Although the present invention is not limited by any particular theory of operation, it is believed that providing an insertion fork 76 with grooved tines that engage ribs on outer surfaces of the legs of the surgical fastener 78 will enhance the stability and control of the surgical fastener when dispensing the surgical fastener from the surgical fastener dispenser 28 (FIGS. 3A and 3B) of the clamping device. In addition, at least a portion of the insertion force is provided closer to the distal ends of the legs 104, 108 of the surgical fastener 78 and not only at the proximal end of the surgical fastener as is the case with prior art fasteners. Providing insertion force on the surgical fastener near the distal end of the fastener may enable smaller and/or lower profile surgical fasteners to be used because, inter alia, the surgical fastener may be inserted using less force.

Figure 6A:
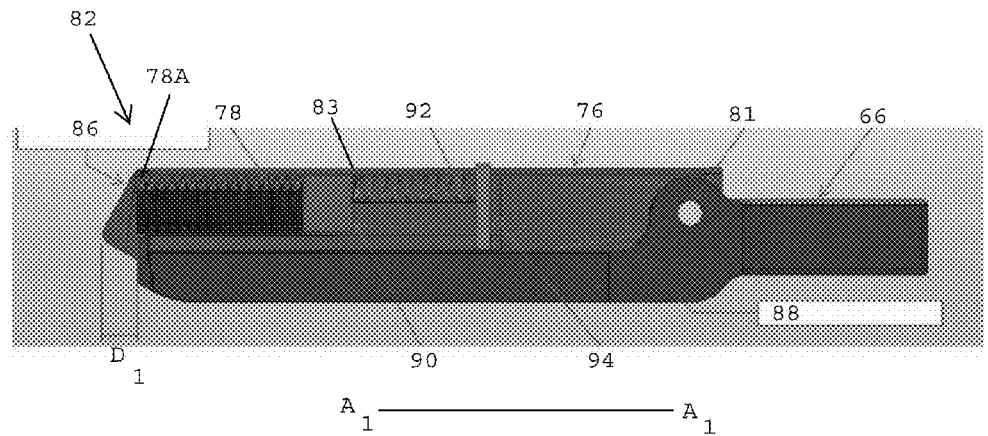
FIGS. 6A-6C show a method of using the surgical fastener dispenser of FIGS. 3A and 3B for deploying a surgical fastener into soft media.
Figure 6B:
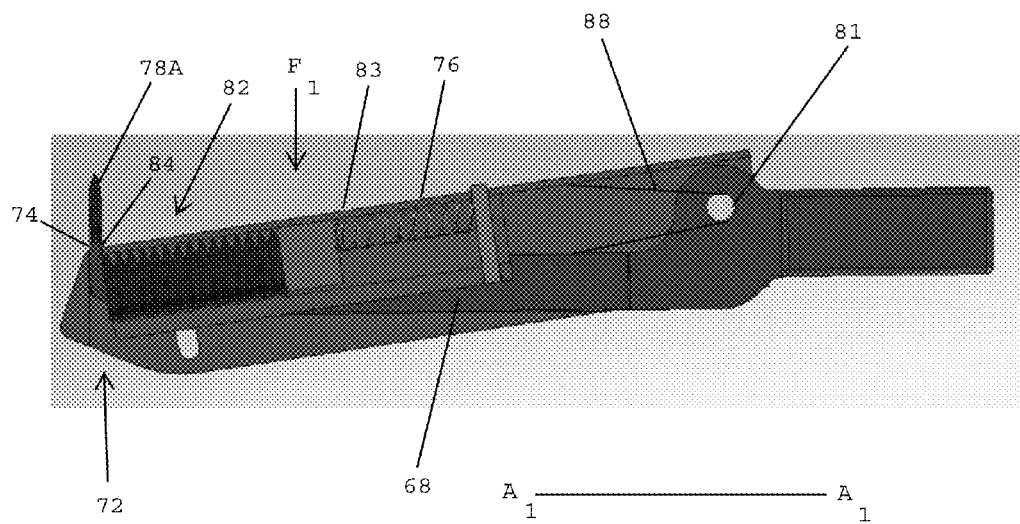
Figure 6C:
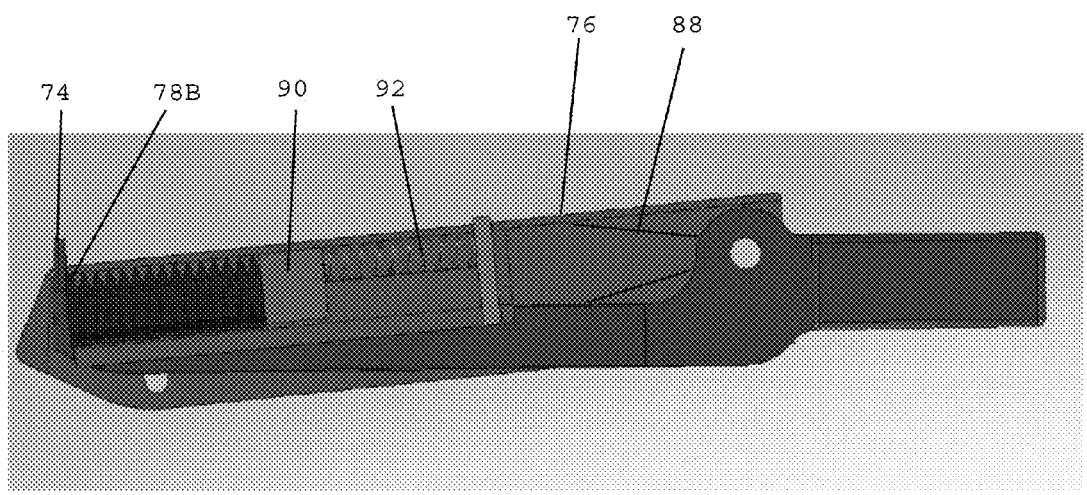

Referring to FIGS. 6A-6C, in one embodiment, the surgical fastener dispenser 28 is adapted for delivering surgical fasteners 78 into soft media, such as tissue. Referring to FIG. 6A, the cartridge return spring 88 normally urges the cartridge body 76 into an initial, undeflected position whereby the top surface 83 of the cartridge body 76 is parallel with the longitudinal axis $A_1$-$A_1$ of the lower arm 22 (FIG. 1). In the initial, undeflected position, none of the surgical fasteners 78 are exposed outside the cartridge body 76. Moreover, the spacer 86 at the distal end 82 of the cartridge body 76 covers the leading surgical fastener 78A mounted on the insertion fork 74. When the cartridge body 76 is in the initial position, the spacer 86 has a leading surface that is preferably spaced a distance $D_1$ from the insertion fork 74, which insures that the surgical fasteners 78, when dispensed, are spaced inwardly from a peripheral edge or seam of a prosthetic device, such as surgical mesh used for repairing a hernia.

Referring to FIG. 6B, in one embodiment, when the clamping device is closed, a downward force $F_1$ is exerted upon the top surface 83 of the cartridge body 76, whereupon the distal end 82 of the cartridge body 76 pivots about pivot pin 81 for moving the cartridge body into a deflected position. In the deflected position, the top surface 83 of the cartridge body 76 defines an angle with the longitudinal axis $A_1$-$A_1$. As the distal end 82 of the cartridge body 76 pivots toward the distal end 72 of the support tray 68, the lead surgical fastener 78A and the upper part of the insertion fork 74 pass through the dispenser opening 84 in the cartridge body 76 and into soft media. The fork 74 preferably stabilizes the exposed surgical fastener 78A for controlling the angle and orientation of the surgical fastener as it is driven into the soft media. As the cartridge body 76 pivots, the cartridge return spring 88 is compressed for storing energy therein. In one embodiment, at the end of a firing cycle, when the downward force $F_1$ is removed, the cartridge return spring 88 returns the cartridge body to the initial, undeflected position shown in FIG. 6A, whereupon the top surface 83 of the cartridge body 76 is parallel with the axis $A_1$-$A_1$.

Referring to FIG. 6C, after the lead surgical fastener has been dispensed from the fork 74, the clamping device 20 (FIG. 1) opens for removing the downward force $F_1$ on the cartridge body 76. When the downward force is removed, the cartridge return spring 88 releases energy stored therein for returning the cartridge body 76 to the initial, undeflected position shown in FIG. 6A. As the cartridge body 76 returns to the undeflected position shown in FIG. 6A, the reload spring 92 urges the advancer 90 to move toward the distal end 82 of the cartridge body 76 for advancing the second surgical fastener 78B into engagement with the insertion fork 74. As the second surgical fastener 78B is loaded onto the insertion fork 74, the cartridge body 76 returns to the initial, undeflected position shown in FIG. 6A. At this stage, the clamping device is ready for another clamping and firing cycle for inserting the second surgical fastener 78B into tissue.

Figure 7:
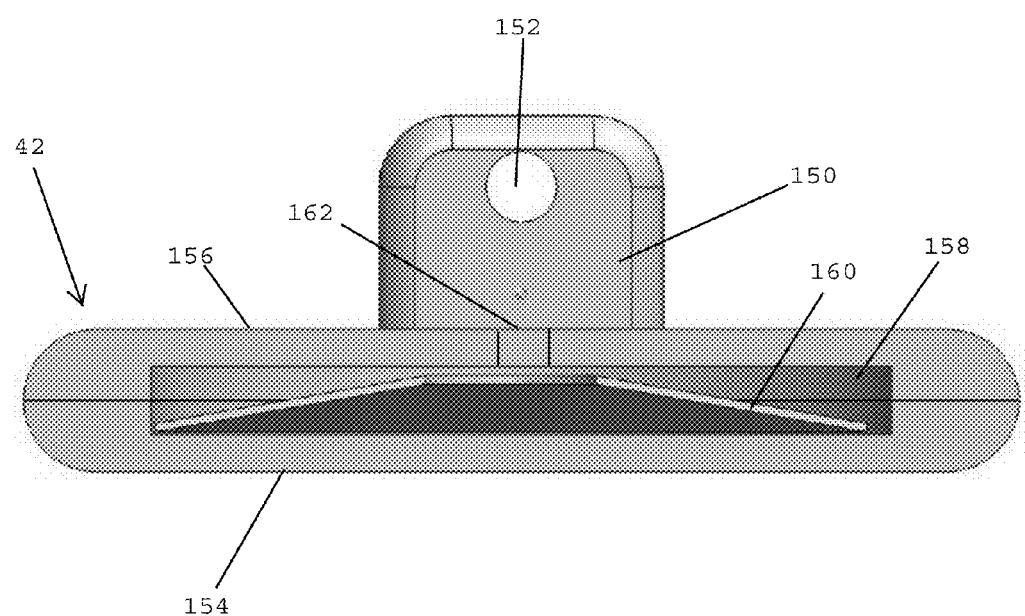
FIG. 7 shows a cross-sectional view of a pad adapted for being pivotally connected to a distal end of the upper arm of the clamping device shown in FIG. 1.

Referring to FIGS. 1 and 7, in one embodiment, the pad 42 is pivotally connected to the distal end 40 of the upper arm 36 of the clamping device 20 via a securing flange 150 having an opening 152 adapted to receive a pivot pin (not shown). The pad 42 desirably includes a bottom surface 154 adapted to oppose the surgical fastener dispenser 28 and a top surface 156 that faces away from the bottom surface. The pad 42 preferably includes an internal cavity 158 adapted to receive a beveled washer 160 that provides tactile feedback (e.g. a clicking sound) when sufficient compression force has been applied by the clamping device 20 for properly delivering a surgical fastener. In one embodiment, the beveled washer 160 desirably produces a clicking sound when compressed, which provides an audible signal to surgical personnel that sufficient compression force has been applied by the clamping device to properly deliver a surgical fastener into tissue. The pad 42 may include an opening 162 formed in the top surface 156 thereof for enabling the clicking sound generated by the washer 160 to pass therethrough.

Figure 8:
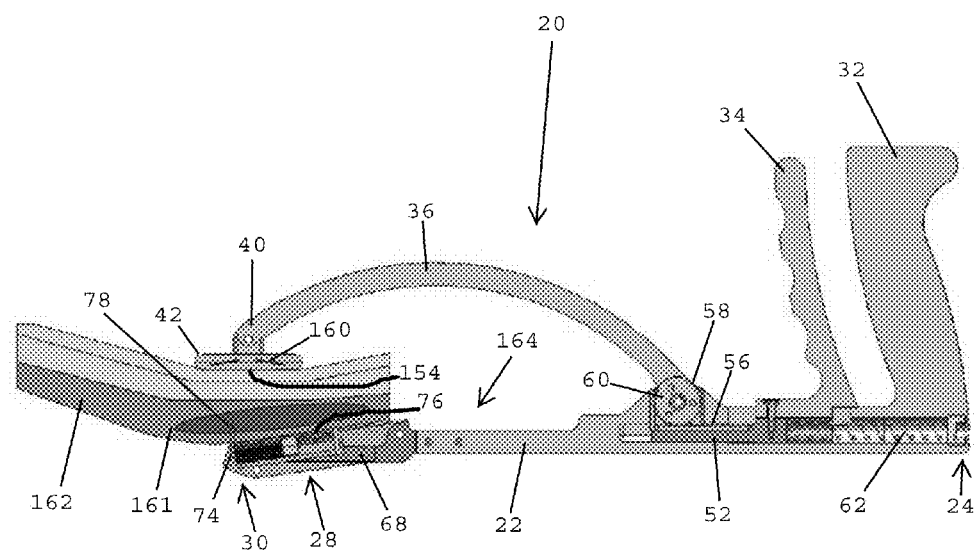
FIG. 8 shows the clamping device of FIG. 1 in a clamping position for dispensing a surgical fastener to secure a surgical mesh to soft media, in accordance with one embodiment of the present invention.

Referring to FIG. 8, in one embodiment, the clamping device 20 may be utilized for securing a prosthetic device, such as a surgical mesh implant 160, to abdominal tissue 162. In one embodiment, a surgical opening 164 is formed in the soft media 162 to access an interior body region of a patient. The surgical mesh 161 is positioned against an interior surface of the abdominal tissue 162. The clamping device 20 may then be used for dispensing surgical fasteners 78 from the surgical fastener dispenser 28 secured to the distal end of the lower arm 22. The surgical fasteners 78 are used for securing the surgical mesh 160 to the soft media 162.

In one embodiment, the lower arm 22 carrying the surgical fastener dispenser 28 is inserted through the surgical opening 164 and into the patient. The upper arm 36 of the clamping device remains outside the patient with the pad 42 opposing the distal end 30 of the surgical fastener dispenser 28. The trigger 34 may be pulled toward the hand grip 32 for sliding the rack 52 toward the proximal end 24 of the lower arm 22. As the rack 52 moves proximally, the rack teeth 56 engage the pinion teeth 58 for rotating the pinion 60 in a counter-clockwise direction, which, in turn, rotates the distal end 40 of the upper arm 36 toward the distal end 30 of the surgical fastener dispenser 28. As the trigger 34 is pulled, the bottom surface 154 of the pad 42 pivots and self-adjusts for engaging the outer surface of the soft media 162. The pivotal connection of the pad 42 with the distal end 40 of the upper arm 36 ensures the bottom surface 154 of the pad 42 remains substantially perpendicular to the vertical orientation of the insertion fork 74 and the surgical fastener 78. The trigger 34 is pulled until sufficient downward force is applied to the cartridge body 76 for deflecting the cartridge body toward the support tray 68 so that the leading surgical fastener 78 may be driven by the insertion fork 74 through the surgical mesh 161 and into the soft media 162. The beveled washer 160 within the pad 42 preferably provides an audible clicking sound when sufficient compression has been applied through the distal ends of the lower arm 22 and the upper arm 36.

After the lead surgical fastener 78 in the surgical fastener dispenser has been dispensed, the trigger 34 may be released. The energy stored in the trigger return spring 62 slides the rack 52 toward the distal end of the lower arm 22, which pivots the distal end 40 of the upper arm 36 away from the distal end 30 of the cartridge assembly 28. The cartridge body 76 is then free to pivot away from the support tray 68 so that the next surgical fastener 78 may be advanced into engagement with the insertion fork 74. The above-described cycle may be repeated for dispensing additional surgical fasteners from the surgical fastener dispenser 28 of the clamping device 20.

Figure 9:
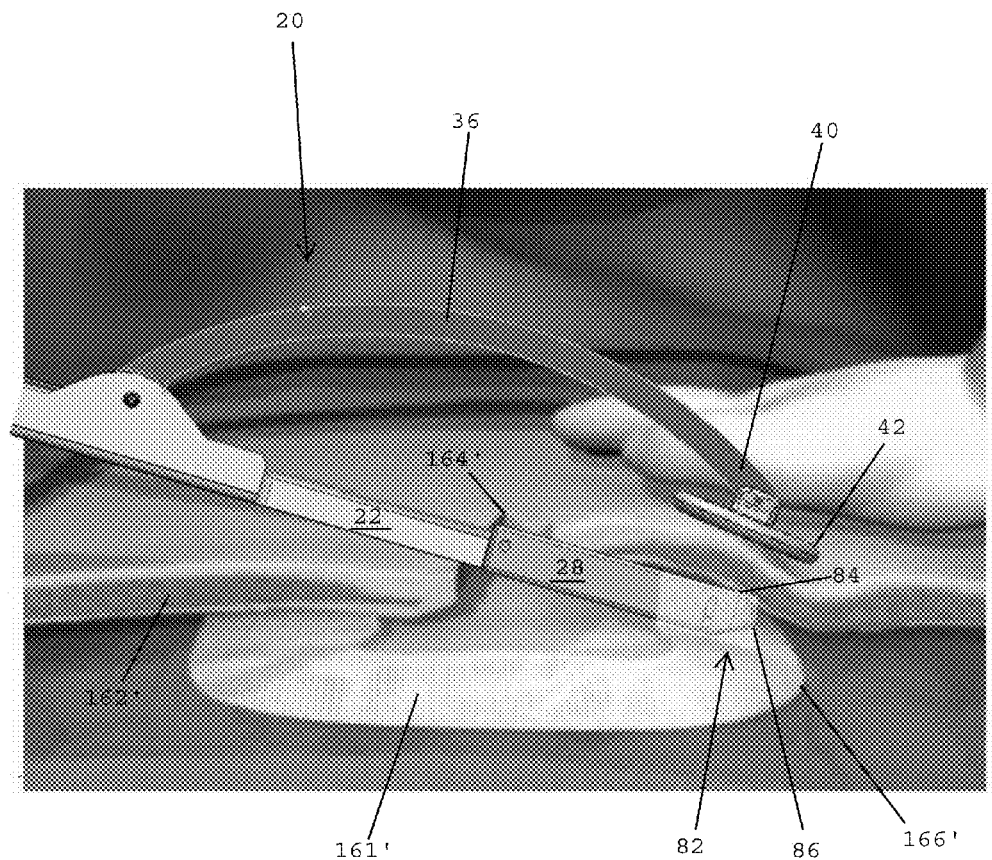
FIG. 9 shows the clamping device of FIG. 1 in a clamping position for securing a skirted mesh to soft media, in accordance with one embodiment of the present invention.

Referring to FIG. 9, in one embodiment, the clamping device 20 may be utilized for securing a skirted surgical mesh 161' to soft media 162'. In FIG. 9, the lower arm 22 and the surgical fastener dispenser 28 are passed through a surgical opening 164'. The spacer 86 on the distal end of the surgical fastener dispenser 28 is advanced through the layers of the skirted surgical mesh 161' until the spacer 86 abuts against the outer peripheral seam of the mesh 161'. The spacer 86 ensures that the opening 84 at the distal end 82 of the surgical fastener dispenser 28 is positioned inside the outer perimeter 166' of the surgical mesh 161'. The trigger of the clamping device 20 may be pulled for pivoting the distal end 40 of the upper arm 36 toward the distal end 82 of the surgical fastener dispenser 28. The upper and lower arms 36, 22 are closed towards one another until sufficient clamping force is applied through the distal ends of the respective arms for depressing the cartridge body on the surgical fastener dispenser for dispensing a surgical fastener. An audible click may be produced by a beveled washer located within the pivoting pad 42 for indicating that sufficient compression has been applied by the clamping device.

The above-described dispensing cycle is repeated until surgical fasteners are dispensed around the entire outer perimeter 166' of the surgical mesh 161'. In one embodiment, the surgical fasteners are spaced no more than two centimeters apart for ensuring that no gaps develop between the surgical mesh 161' and the soft media 162'.

Figure 10:
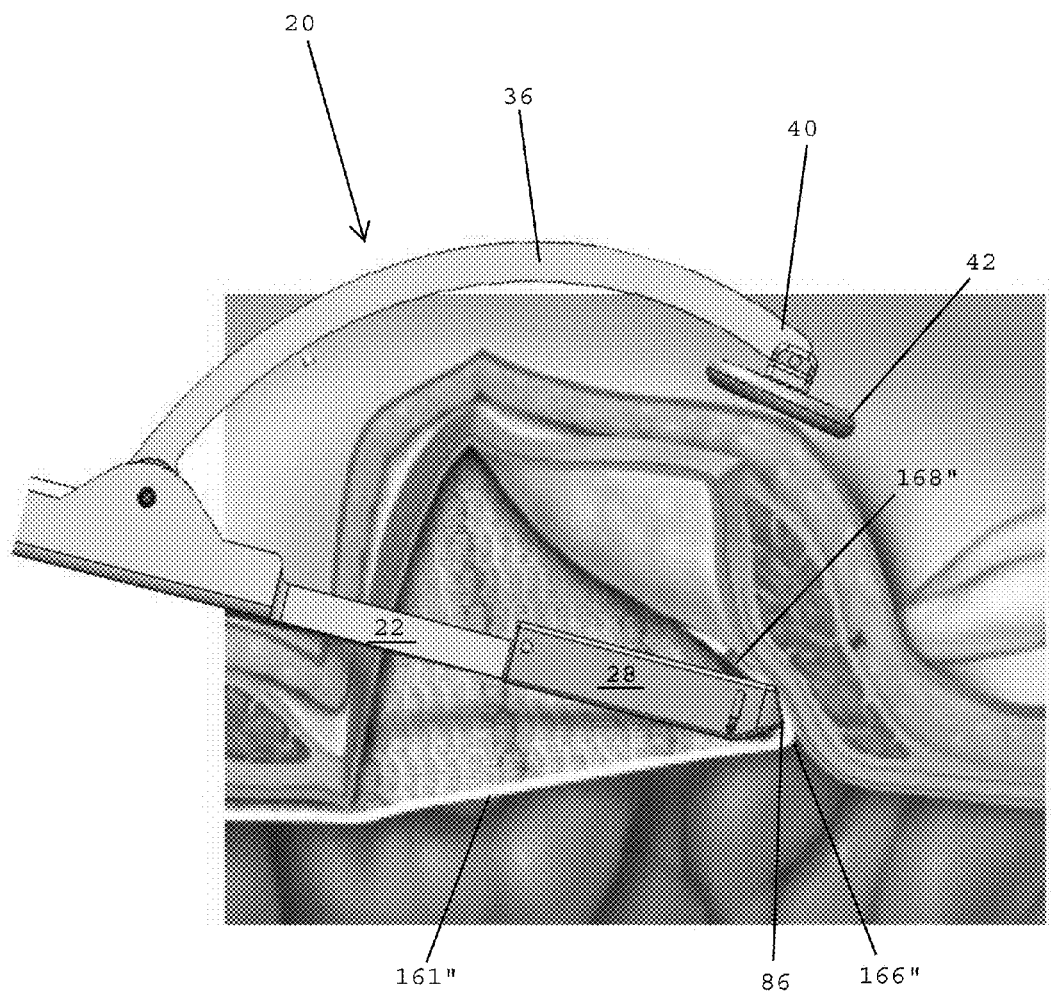
FIG. 10 shows the clamping device of FIG. 1 in an open, ready to fire position during a surgical procedure for securing a flat surgical mesh to soft media, in accordance with one embodiment of the present invention.

Referring to FIG. 10, in one embodiment, the clamping device 20 is used on a surgical mesh 161" having a folded over edge 168". The cartridge assembly is preferably advanced between the surgical mesh 161" and the folded over edge 168" until the spacer 86 abuts against the outer peripheral edge 166" of the surgical mesh 161". The clamping device 20 may be closed so that the distal end 40 of the upper arm 36 pivots toward the surgical fastener dispenser 28 attached to the distal end of the lower arm 22. Compression forces are applied through the distal ends of the respective lower and upper arms 22, 36 until a surgical fastener is dispensed from the surgical fastener dispenser 28. Surgical personnel may discern when sufficient compression forces have been applied for dispensing a surgical fastener when an audible click is produced by a beveled washer disposed within the pivotally-connected pad 42. The above-described process is preferably repeated around the outer periphery 166" of the surgical mesh 161" for dispensing a plurality of fasteners around the outer periphery of the mesh.

Figure 11A:
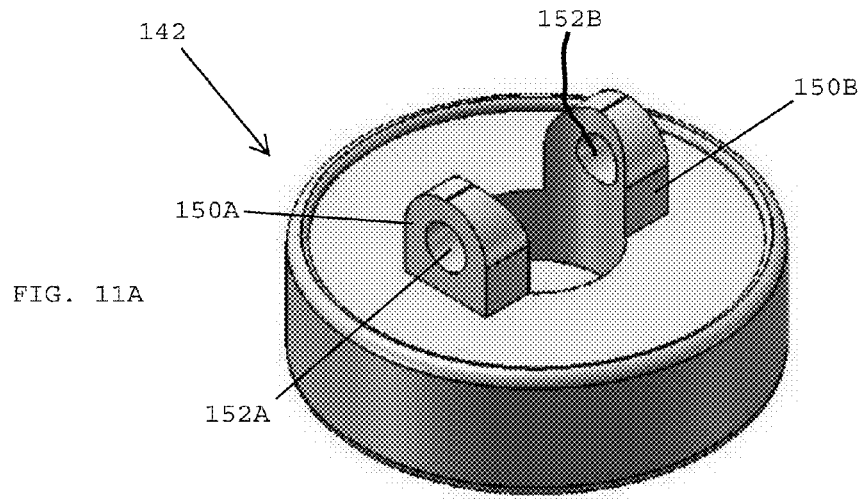
FIGS. 11A-11C show a pad having a marker, the pad being pivotally connectible to a distal end of the upper arm of the clamping device shown in FIG. 1, in accordance with one embodiment of the present invention.
Figure 11B:
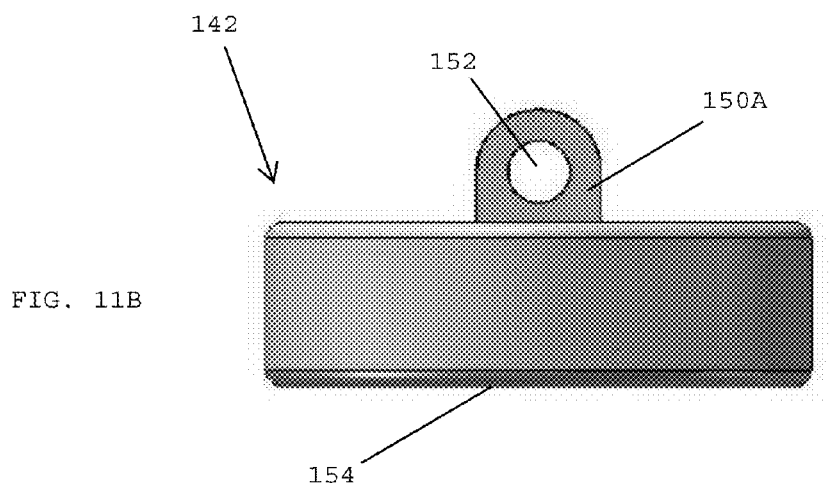
Figure 11C:
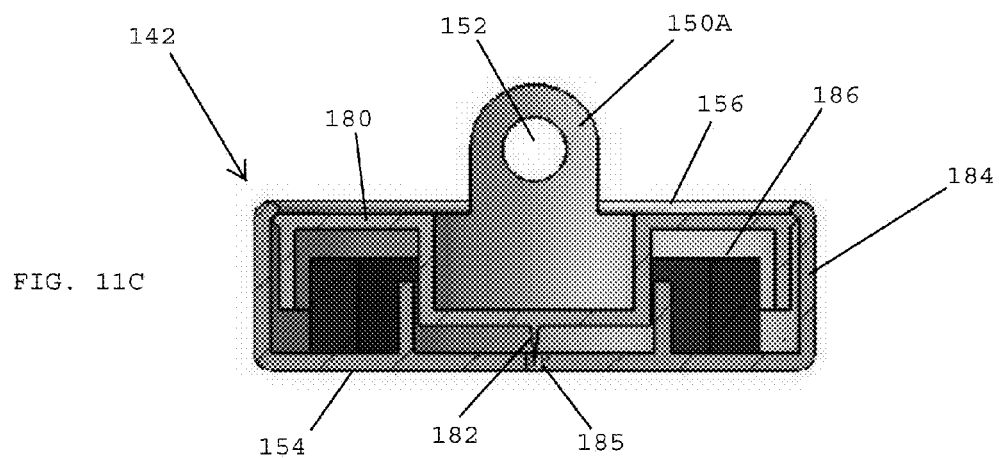

Referring to FIGS. 11A-11C, in one embodiment, a pad 142 is adapted for being pivotally connected to the distal end 40 of the upper arm 36 of the clamping device 20 shown in FIGS. 1 and 2. The pad 142 desirably includes a pair of flanges 150A, 150B having aligned openings 152A, 152B passing therethrough that are adapted to receive a pivot pin for pivotally connecting the pad 142 with the distal end 40 of the upper arm 36 (FIG. 1).

Referring to FIG. 11B, the pad 142 preferably includes a bottom surface 154 adapted to abut against an outer surface of soft media, such as the patient's outer skin surface. Referring to FIG. 11C, in one embodiment, the pad 142 preferably includes an inner part 180 secured to the flange 150A, 150B. The inner part 180 includes a marker 182 provided at a lower end thereof. The marker 182 may be an ink marker adapted to form an ink marking on a patient's skin surface. The pad 142 preferably includes a lower part 184 that extends around the upper part 180. The lower part 184 includes the bottom surface 154 of the pad 142. The bottom surface 154 preferably includes an opening 185 formed therein that enables the marker 182 to pass therethrough. When compression forces are applied to the bottom surface 154 of the lower member 184, the bottom surface 154 of the lower member 184 preferably slides toward the top surface 156 of the upper member 180 so that the marker 182 projects through the opening 185 in the bottom surface 154 for marking a surface. The pad 142 preferably includes a stop 186 and halts further sliding movement of the bottom surface 154 toward the top surface 156.

When a surgical fastener is applied using the clamping device disclosed herein, the bottom surface 154 of the pad 142 desirably opposes the distal end of the cartridge body from which the surgical fastener is dispensed. The marker 182 is preferably aligned with the opening 84 provided at the distal end 82 of the cartridge body 76. The indicia provided on the patient's skin surface by the marker 182 provides an exact mirror image of where the surgical fastener has been inserted into soft media. Thus, surgical personnel are provided with an accurate methodology for keeping track of how many surgical fasteners have been dispensed and the exact location of each surgical fastener.

Figures 12A, 12B:
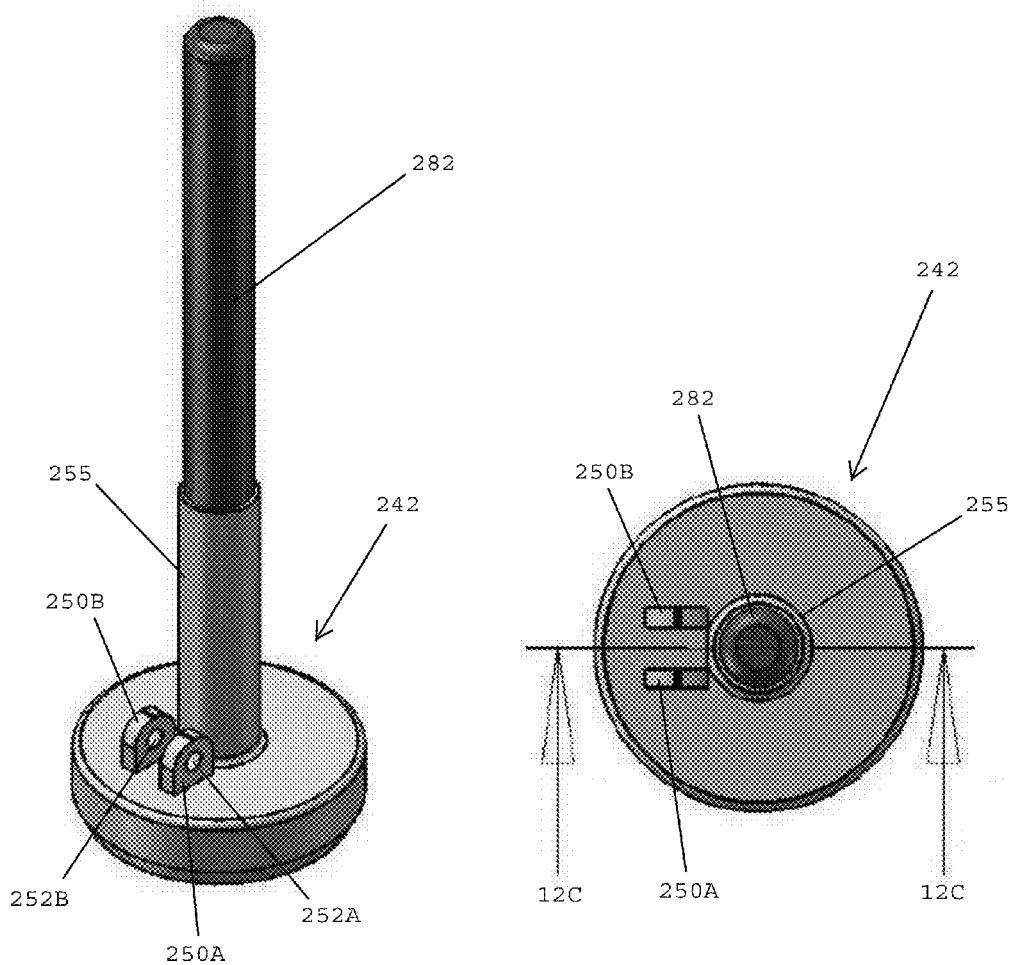
FIGS. 12A-12C show a pad having a marker, the pad being pivotally connectible to a distal end of the upper arm of the clamping device shown in FIG. 1, in accordance with another embodiment of the present invention.
Figure 12C:
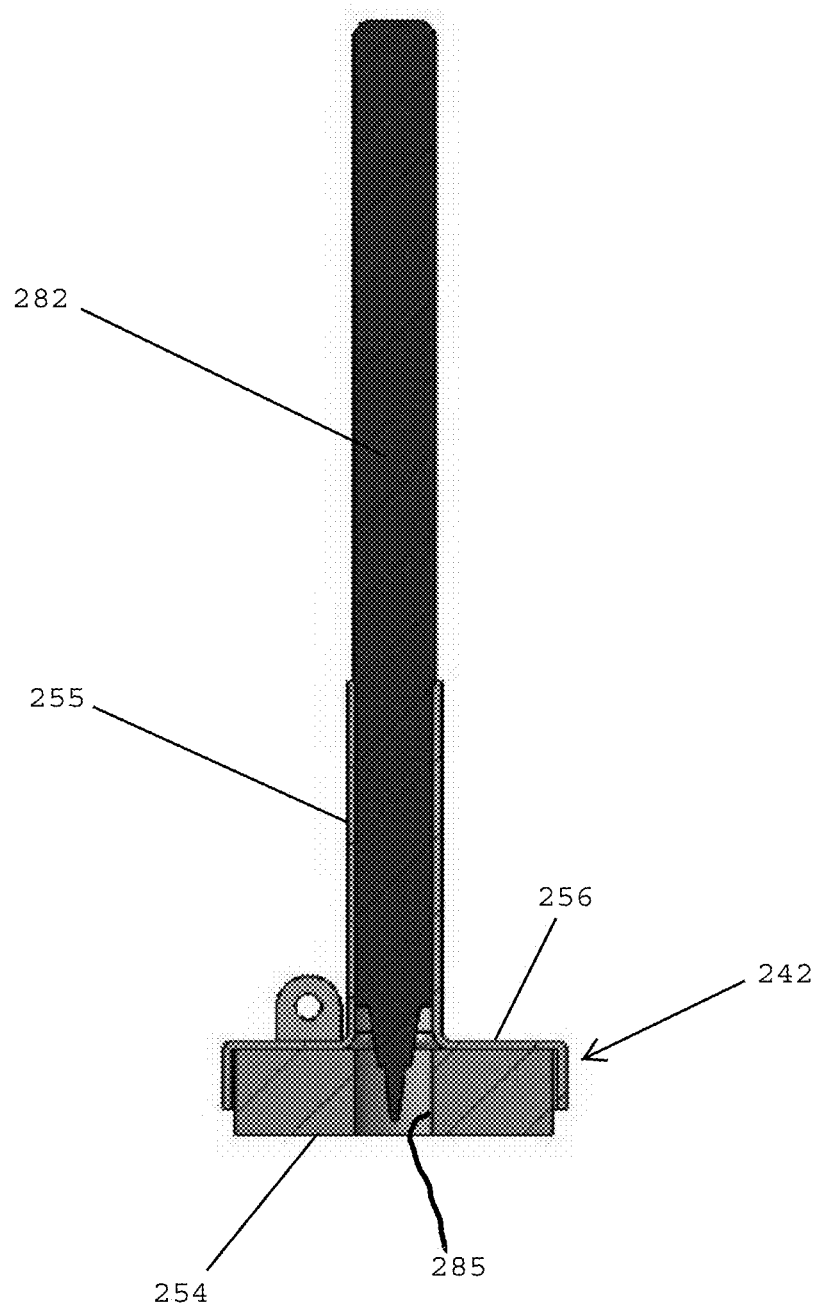

FIGS. 12A-12C show another pad 242 having a marker 282 that may be utilized for marking a patient's skin surface to indicate where a surgical fastener has been inserted into the patient's tissue. Referring to FIGS. 12A and 12B, the pad 242 preferably includes a pair of securing flanges 250A, 250B having aligned openings 252A, 252B, respectively, that are adapted to receive a pivot pin for securing the pad 242 to a distal end of the upper arm of the clamping device shown in FIGS. 1 and 2. The pad 242 preferably includes a tube 255 that is adapted to receive a marker 282.

FIG. 12C shows the marker 282 inserted into the tube 255 of the pad 242. The pad 242 has a bottom surface 254, a top surface 256 and an opening 285 that extends between the bottom and top surfaces 254, 256. The lower end of the marker 282 preferably extends into the opening 285 for making markings on a patient's skin surface when the pad 242 is compressed against the patient's skin surface. As noted above, the marker 282 provides an efficient and highly-accurate methodology for identifying where a surgical fastener has been inserted into a patient's tissue, and for indicating the total number of surgical fasteners inserted into the patient's tissue.

Figure 13:
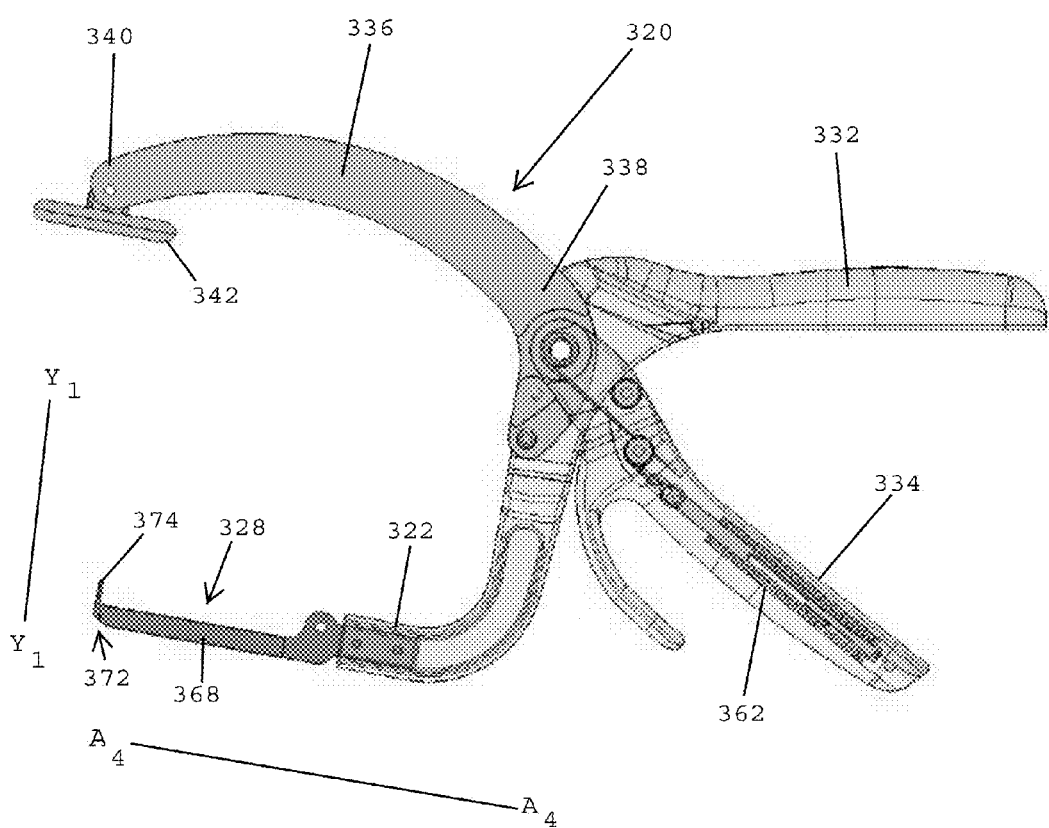
FIG. 13 shows a clamping device for dispensing surgical fasteners including a lower arm and an upper arm, in accordance with another embodiment of the present invention.

Referring to FIG. 13, in one embodiment, a clamping device 320 for dispensing surgical fasteners preferably includes a lower arm 322 that extends along a longitudinal axis $A_4$-$A_4$ and a surgical fastener dispenser 328 secured to the distal end of the lower arm 322. The surgical fastener dispenser 328 includes a support tray 368 having a distal end 372 including a fork 374 adapted for driving surgical fasteners into soft media. The insertion fork 374 preferably extends along an axis $Y_1$-$Y_1$ that is substantially perpendicular to the longitudinal axis $A_4$-$A_4$ of the lower arm 322 and the support tray 368. The lower arm 322 is preferably coupled with a hand grip 332.

The clamping device 320 preferably includes an upper arm 336 that is pivotally connected with the lower arm 322. The upper arm 336 has a proximal end 338 pivotally coupled with the lower arm 322 and a distal end 340 remote therefrom. A pad 342 is pivotally connected with the distal end 340 of the upper arm 336. The upper arm 336 is desirably connected with a trigger 334.

In operation, the trigger 334 may be pulled toward the handle 332 for moving the distal end 340 of the upper arm 336 toward the distal end 372 of the support tray 368. The trigger 334 preferably includes an internal extension spring 362 that is installed under a load that is delivered via a cable system through the arms until sufficient compression of the arms has been attained. At that point, further pulling of the trigger 334 toward the handle 332 will not result in additional compression forces being exerted through the distal ends of the upper and lower arms. Instead, the internal extension spring 362 continues to extend.

Figure 14A:
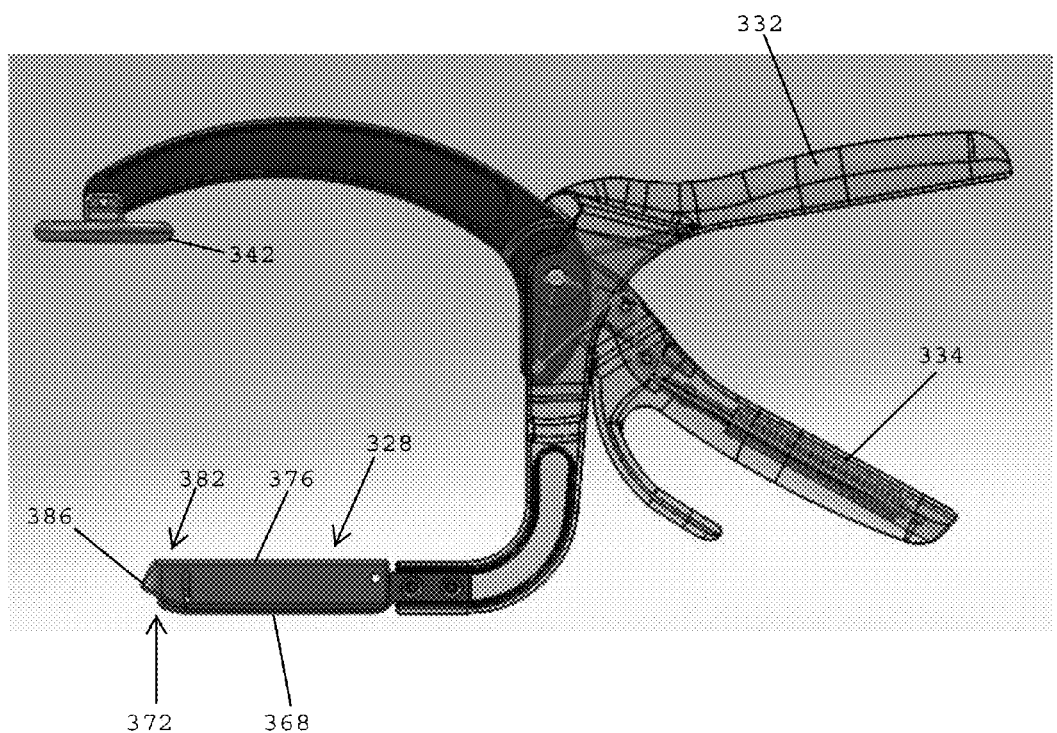
FIG. 14A shows the clamping device of FIG. 13 with a surgical fastener dispenser secured to a distal end of the lower arm and a force limiting mechanism installed in the lower handle that is engaged with the upper arm, in accordance with one embodiment of the present invention.

Referring to FIG. 14A, in one embodiment, the surgical fastener dispenser 328 preferably includes a cartridge body 376 that is pivotally coupled with the support tray 368. The cartridge body 376 preferably has a spacer 386 at a distal end thereof that projects beyond the distal end 372 of the support tray 368. The cartridge body 376 preferably has a plurality of surgical fasteners (not shown) loaded therein. During a firing cycle, when the trigger 334 is pulled toward the hand grip 332, compression forces are applied between the pad 342 and the surgical fastener dispenser 328 until one of the surgical fasteners is dispensed from a dispenser opening at the distal end 382 of the cartridge body 376.

Figure 14B:
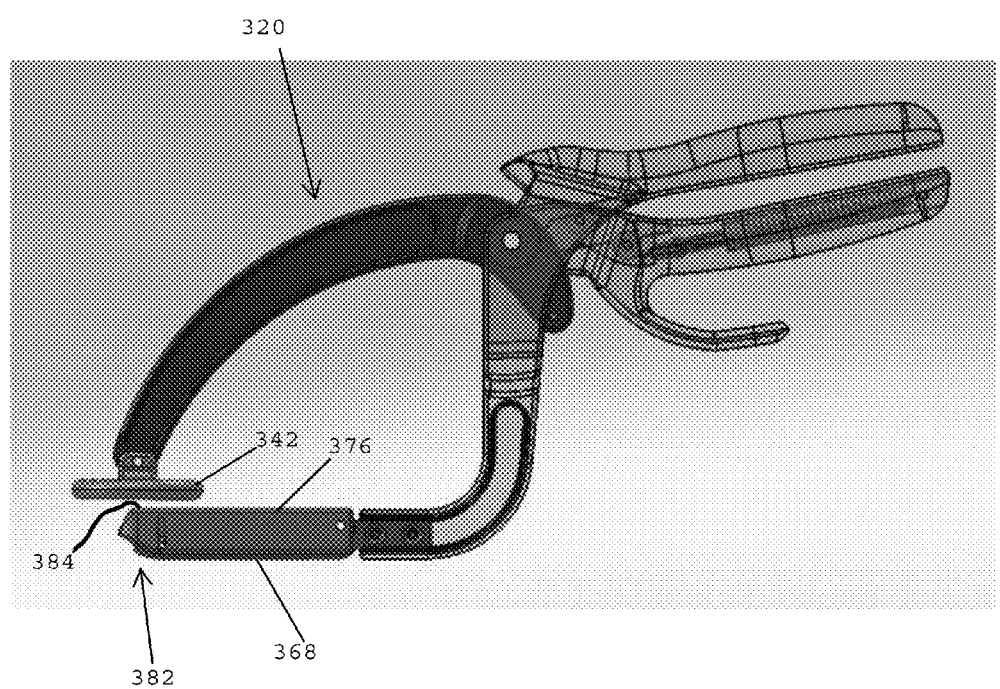
FIG. 14B shows the clamping device of FIG. 14A in a closed position for dispensing a surgical fastener into soft media, in accordance with one embodiment of the present invention.

FIG. 14B shows the clamping device 320 in a closed position with the pivotally connected pad 342 opposing the dispenser opening 384 at the distal end 382 of the cartridge body 376. As soft media is compressed between the pad 342 and the cartridge body 376, the distal end 382 of the cartridge body 376 pivots in a downward direction toward the support tray 368 until the insertion fork at the distal end of the support tray 368 pushes a lead surgical fastener through the dispenser opening 384 for insertion into soft media.

Other embodiments of the present invention may include linkages that vary from the linear mechanism shown in FIGS. 1 and 2 of the present application. In these alternative embodiments, the handle elements pivot relative to one another while the upper and lower arms move toward and away from one another in a linear or parallel fashion. FIGS. 15-18 are schematic drawings that show only the linkages coupling the upper and lower arms and the pivoting handles. Although not shown, it is contemplated that the embodiments shown in FIGS. 15-18 may include one or more of the features shown and described above for FIGS. 1-10.

Figure 15:
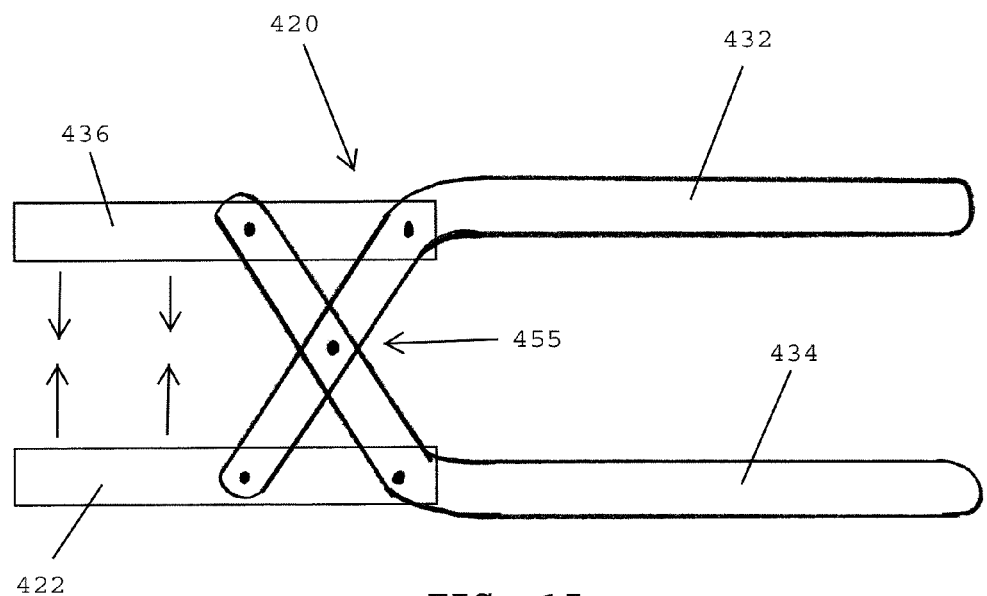
FIG. 15 shows a schematic view of a clamping device including a lower arm and an upper arm joined by a scissor-jack mechanism and having in-line handles, in accordance with one embodiment of the present invention.

Referring to FIG. 15, in one embodiment, a clamping device 420 for dispensing surgical fasteners into soft media preferably includes a lower arm 422 and an upper arm 436 that are joined together with a scissor-jack linkage 455. The clamping device 420 has first and second handles 432, 434 that are in-line with the respective lower and upper arms 422, 436. As the first and second handles 432, 434 pivot toward one another for closing the clamping device 420, the scissor-jack linkage moves the lower and upper arms 422, 436 toward one another in a linear or parallel fashion for dispensing a lead surgical fastener (e.g., see FIG. 6B).

Figure 16:
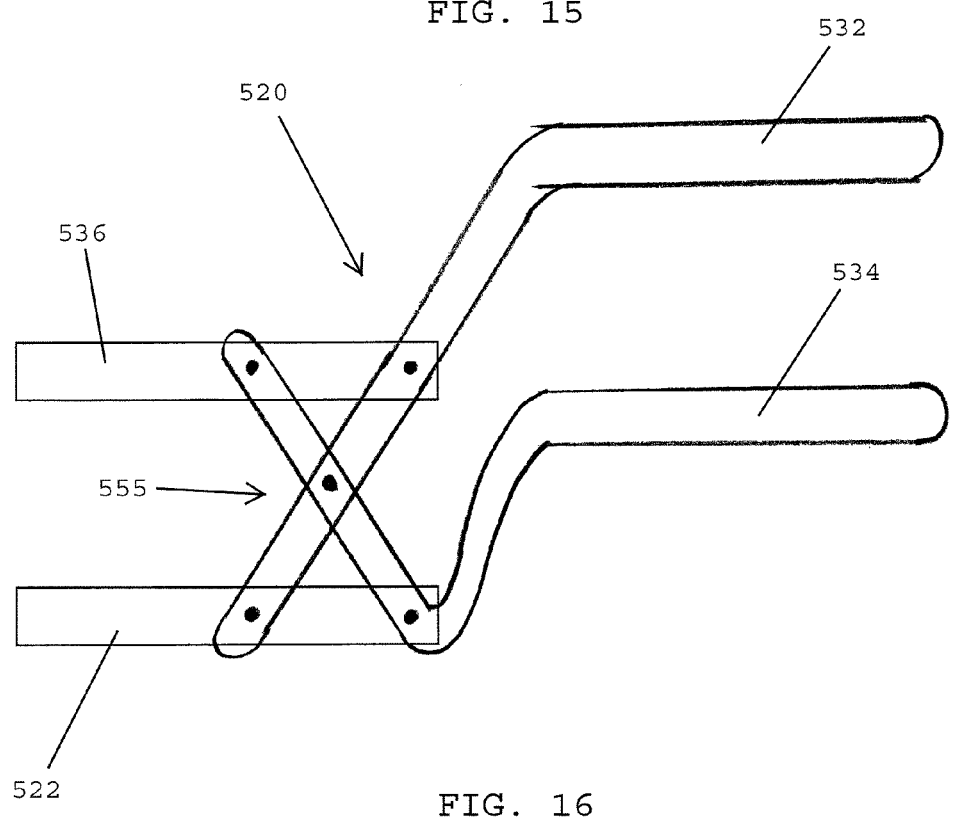
FIG. 16 shows a schematic view of a clamping device including a lower arm and an upper arm joined by a scissor-jack mechanism and having offset handles, in accordance with one embodiment of the present invention.

Referring to FIG. 16, in one embodiment, a clamping device 520 for dispensing surgical fasteners into soft media preferably includes a lower arm 522 and an upper arm 536 that are joined together with a scissor-jack linkage 555. The clamping device 520 has first and second handles 532, 534 that are offset from the lower and upper arms 522, 536, respectively. As the first and second handles 532, 534 pivot toward one another for closing the clamping device 520, the scissor-jack linkage moves the lower and upper arms 522, 536 toward one another in a linear (i.e., parallel) fashion for dispensing a lead surgical fastener (e.g., see FIG. 6B).

Figure 17:
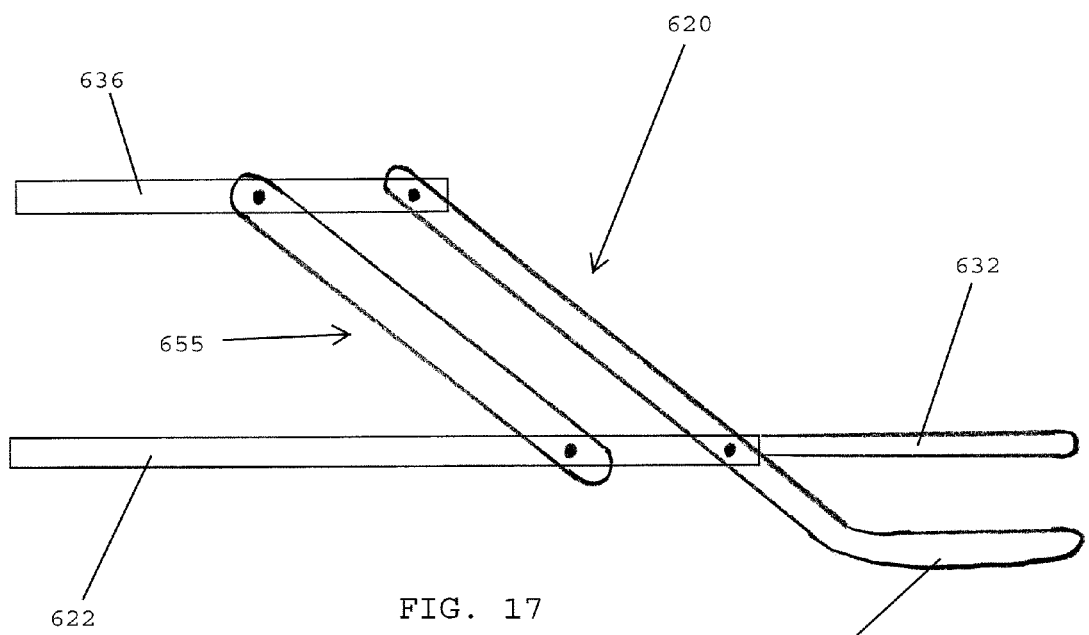
FIG. 17 shows a schematic view of a clamping device including a lower arm and an upper arm joined by a parallel link mechanism, in accordance with one embodiment of the present invention.

Referring to FIG. 17, in one embodiment, a clamping device 620 for dispensing surgical fasteners into soft media preferably includes a lower arm 622 and an upper arm 636 that are joined together with a parallel link arrangement 655. The clamping device 620 has first and second handles 632, 634 that are adapted to pivot relative to one another. As the first and second handles 632, 634 pivot toward one another for closing the clamping device 620, the parallel link arrangement 655t moves the lower and upper arms 622, 636 toward one another in a parallel fashion for dispensing a lead surgical fastener (e.g., see FIG. 6B).

Figure 18:
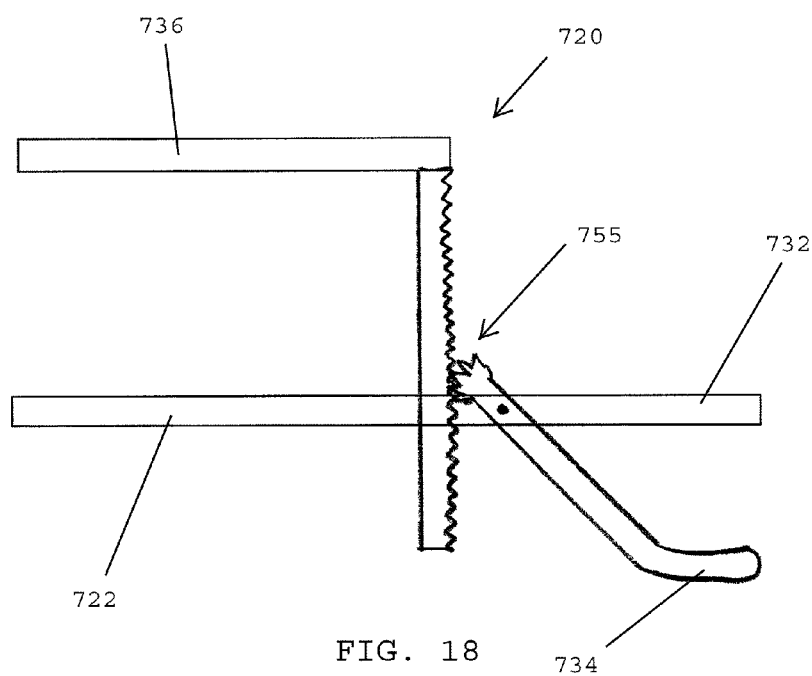
FIG. 18 shows a schematic view of a clamping device including a lower arm and an upper arm joined by a rack and pinion gear mechanism, in accordance with one embodiment of the present invention.

Referring to FIG. 18, in one embodiment, a clamping device 720 for dispensing surgical fasteners into soft media preferably includes a lower arm 722 and an upper arm 736 that are joined together with a rack and pinion gear mechanism 755. The clamping device 720 has first and second handles 732, 734 that are adapted to pivot relative to one another. As the first and second handles 732, 734 pivot toward one another for closing the clamping device 720, the rack and pinion gear mechanism 755 moves the lower and upper arms 722, 736 toward one another in a parallel fashion for dispensing a lead surgical fastener (e.g., see FIG. 6B).

The linkages shown and described herein are not the only types of mechanisms that can be used to provide linear motion between the upper and lower arms of the clamping device.

Other embodiments may have a scissor-jack mechanism with a plurality of linkages resembling an accordion-like system. In one embodiment, a worm gear mechanism may be employed. In these embodiments, the handle elements desirably pivot toward and away from one another as the upper and lower arms move in a linear/parallel fashion.

In one embodiment, sliding guides may be used to move an upper arm and an upper handle connected thereto toward a lower arm and a lower handle connected thereto, while maintaining linear/parallel movement between the upper and lower arms. In this embodiment, the upper arm/upper handle component moves in a linear/parallel fashion relative to the lower arm/lower handle.

In one embodiment, a marking assembly as described above is FIGS. 11A-11C and 12A-12C may be secured to the distal end of an arm coupled with an applicator instrument having a handle and an elongated tube for dispensing surgical fasteners. Referring to FIGS. 19A-19C, in one embodiment, a device 820 for dispensing surgical fasteners into tissue preferably includes a tubular member 822 having a proximal end 824, a distal end 826, and a surgical fastener dispenser opening 828 at the distal end that is adapted for dispensing surgical fasteners into tissue. The dispensing device 820 preferably includes a handle 830 secured to the proximal end 824 of the tubular member 822 and an actuator (not shown) that may be engaged for dispensing a surgical fastener from the surgical fastener dispenser opening 828 at the distal end of the tubular member 822. In one embodiment, a surgical fastener is dispensed each time the actuator is engaged. The dispensing device 820 may incorporate one or more features of applicator instruments disclosed in commonly assigned U.S. patent application Ser. Nos. 12/464,143; 12/464,151; 12/464, 165; and 12/464,177, the disclosures of which are hereby incorporated by reference herein.

In one embodiment, the dispensing device 820 preferably includes an upper arm 836 having a proximal end 838 and a distal end 840. The distal end 840 of the upper arm 836 is preferably adapted to swing away from and toward the surgical fastener dispenser opening 828 at the distal end 826 of the tubular member 822. In one embodiment, the proximal end 838 of the upper arm 836 is pivotally secured to the handle 830. In one embodiment, the upper arm 836 defines an arc or curve. The dispensing device 820 desirably includes a marking assembly 842 connected to the distal end 838 of the upper arm 836. The marking assembly 842 is moveable away from and toward the surgical fastener dispenser opening 828 adjacent the distal end of the tubular member 822.

In operation, the distal end 826 of the dispensing device 820 is inserted into a surgical opening for dispensing surgical fasteners through the surgical fastener dispenser opening 828 and into tissue for securing an implant to the tissue. In one embodiment, each time the trigger on the housing 830 is pulled, the marking assembly 842 at the distal end 838 of the upper arm 836 is moved toward the distal end of the tubular member 822 and into alignment with the surgical fastener dispenser opening 828 for marking a location on the external surface that mirrors where the surgical fastener has been positioned inside the surgical opening.

Referring to FIGS. 20A-20O, in one embodiment, a device 920 for dispensing surgical fasteners into tissue preferably includes a tubular member 922 having a proximal end 924 and a distal end 926 having a surgical fastener dispenser opening 928 at the distal end that is adapted for dispensing surgical fasteners into tissue. The dispensing device 920 preferably includes a handle 930 secured to the proximal end 924 of the tubular member 922 and an actuator (not shown), such as a trigger, that may be engaged for dispensing a surgical fastener from the surgical fastener dispenser opening 928 at the distal end of the tubular member 922. In one embodiment, a surgical fastener is dispensed each time the actuator on the handle 930 is engaged.

In one embodiment, the dispensing device 920 preferably includes an upper arm 936 having a proximal end 938 and a distal end 940. The upper arm 936 may be flexible so that the distal end 940 of the upper arm may move away from and toward the surgical fastener dispenser opening 928 at the distal end of the tubular member 922. In one embodiment, the proximal end 938 of the upper arm 936 is secured to the handle 930 via a pivotal connection. In one embodiment, the upper arm 936 defines an arc or curve. The dispensing device 920 desirably includes a marking assembly 942 connected to the distal end 938 of the upper arm 936. In one embodiment, the marking assembly 942 is pivotally secured to the distal end 940 of the upper arm 936. The marking assembly is moveable away from and toward the surgical fastener dispenser opening 928 adjacent the distal end of the tubular member 922 for marking an exterior surface as described above for the dispensing and marking device shown in FIGS. 19A-19C.

Figures 21A, 21B, 21C:
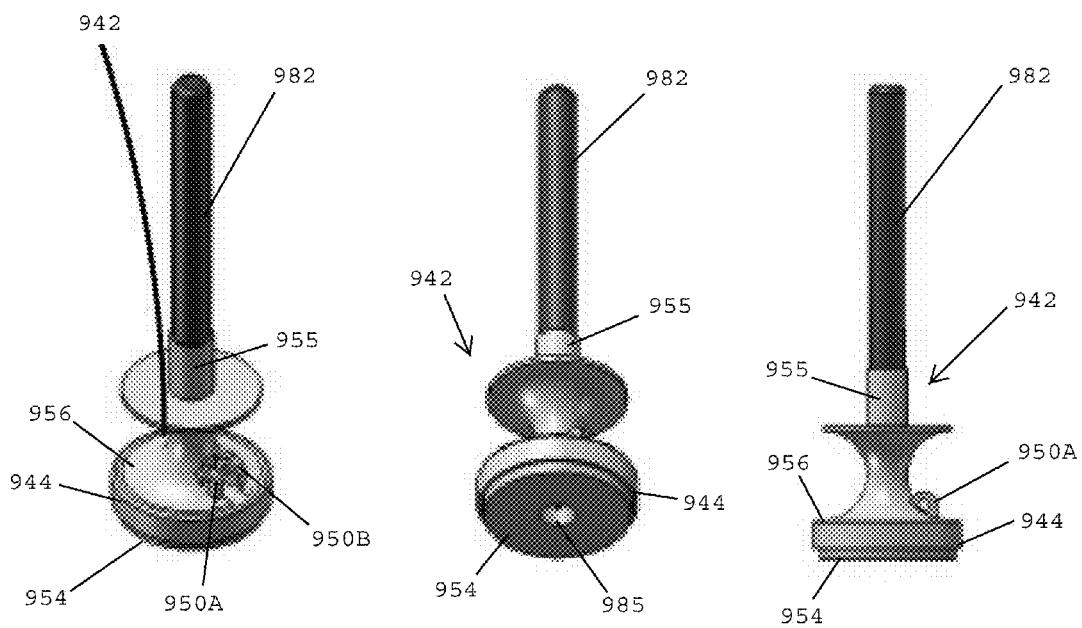
FIGS. 21A-21C show a marking assembly, in accordance with one embodiment of the present invention.

Referring to FIGS. 21A-21C, in one embodiment, a marking assembly 942 includes a base 944 and a pair of securing flanges 950A, 950B having aligned openings that are adapted to receive a pivot pin for securing the base 944 to the distal end of the upper arm 936 of the dispensing device 920 shown in FIGS. 20A-20O. The marking device 942 preferably includes a tube 955 extending upwardly from the base 944 that is adapted to receive a marker 982.

In one embodiment, the base 944 has a bottom surface 954, a top surface 956 and an opening 985 that extends between the bottom and top surfaces 954, 956. The lower end of the marker 982 is preferably accessible at the lower end of the opening 985 for generating markings on a patient's skin surface when the base 944 is pressed against the patient's skin surface. As noted above, the marker 982 provides an efficient and highly-accurate methodology for identifying where a surgical fastener has been inserted into a patient's tissue, and for indicating the total number of surgical fasteners inserted into the patient's tissue.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A device for dispensing surgical fasteners inside a body and generating marks outside the body indicating where said surgical fasteners have been dispensed inside the body, said device comprising:
a first member having a surgical fastener dispenser with a surgical fastener dispenser opening at a distal end thereof adapted for dispensing surgical fasteners;
a plurality of surgical fasteners loaded in series in said surgical fastener dispenser for being dispensed one at a time from said surgical fastener dispenser opening, wherein said surgical fastener dispenser includes a surgical fastener advancer that urges said surgical fasteners distally toward said surgical fastener dispenser opening;
a second member coupled with said first member, said second member having a distal end that opposes said surgical fastener dispenser opening;
a marking assembly secured to the distal end of said second member, wherein said marking assembly is moveable away from and toward said surgical fastener dispenser opening, and wherein said marking assembly is adapted for generating marks on an external surface that mirror the location of each said surgical fastener dispensed from said surgical fastener dispenser opening at the distal end of said first member.

2. The device as claimed in claim 1, wherein said surgical fastener dispenser opening is adapted for insertion into a surgical opening formed in the body for dispensing said surgical fasteners into tissue inside the surgical opening with said marking assembly positioned outside the surgical opening and over the external surface.

3. The device as claimed in claim 1, wherein said first member comprises a lower arm having a distal end including said surgical fastener dispenser opening, and wherein said second member comprises an upper arm having a proximal end that is coupled with said lower arm via a pivotal connection.

4. The device as claimed in claim 3, wherein said surgical fastener dispenser is secured to the distal end of said lower arm, said surgical fastener dispenser further comprising an insertion fork that engages a leading one of said surgical fasteners for dispensing said leading surgical fastener through said surgical fastener dispenser opening.

5. The device as claimed in claim 4, further comprising an actuator coupled with said upper and lower arms for selectively moving said arms between an open position in which said marking assembly is spaced from said surgical fastener dispenser and a closed position in which said marking assembly is closer to said surgical fastener dispenser for clamping tissue between said marking assembly and said surgical fastener dispenser, wherein after said insertion fork has dispensed the leading one of said surgical fasteners through said surgical fastener dispenser opening, said surgical fastener advancer spring advances the next one of said surgical fasteners into alignment with said insertion fork.

6. The device as claimed in claim 4, wherein said surgical fastener dispenser is adapted for insertion into the surgical opening while said marking assembly remains outside the surgical opening.

7. The device as claimed in claim 4, wherein said marking assembly comprises a marker adapted to contact the external surface outside the surgical opening for generating the marks on the external surface for mirroring said surgical fasteners dispensed into the tissue inside the surgical opening.

8. The device as claimed in claim 7, wherein said marker is adapted to generate a visible pattern of the marks on the external surface indicating the number and location of said surgical fasteners dispensed into the tissue inside the surgical opening.

9. The device as claimed in claim 7, wherein said marker is selected from the group of markers consisting of a pen, a felt marker, a pencil, a crayon, a needle, and a thorn.

10. The device as claimed in claim 7, wherein said marking assembly comprises:
a pad connected to the distal end of said upper arm;
said pad having a bottom surface adapted to apply a clamping force;
an opening formed in said bottom surface of said pad;

said marker being coupled with said pad and having a marking surface accessible through said opening formed in said bottom surface of said pad for marking the external surface.

11. The device as claimed in claim 10, wherein when said device is closed said bottom surface of said pad applies the clamping force upon the external surface which, in turn, applies a clamping force through the tissue onto said surgical fastener dispenser for dispensing one of said surgical fasteners from said surgical fastener dispenser opening and into the tissue inside the surgical opening.

12. The device as claimed in claim 4, wherein said marking assembly opposes said surgical fastener dispenser opening and is pivotally secured to the distal end of said upper arm.

13. The device as claimed in claim 1, wherein said first member is an elongated tube having said surgical fastener dispenser opening at the distal end thereof and said second member has a proximal end coupled with said first member and a distal end that opposes said surgical fastener dispenser opening.

14. The device as claimed in claim 13, wherein said device further comprises a handle connected with a proximal end of said elongated tube, and wherein said second member is secured to said handle.

15. The device as claimed in claim 14, wherein said second member is flexible for moving the distal end of said second member toward and away from said surgical fastener dispenser opening at the distal end of said elongated tube.

16. A device for dispensing surgical fasteners into tissue inside a surgical opening while simultaneously generating marks on an external surface outside the surgical opening, said device comprising:
a lower arm having a proximal end and a distal end including a surgical fastener dispenser having a surgical fastener dispenser opening adapted for dispensing surgical fasteners;
a plurality of surgical fasteners loaded in series in said surgical fastener dispenser for being dispensed one at a time from said surgical fastener dispenser opening, wherein said surgical fastener dispenser includes a surgical fastener advancer spring that urges said surgical fasteners distally toward said surgical fastener dispenser opening;
an upper arm coupled with said lower arm and having a distal end that opposes said surgical fastener dispenser opening at the distal end of said lower arm;
a marking assembly secured to the distal end of said upper arm and opposing said surgical fastener dispenser opening at the distal end of said lower arm;
wherein the distal ends of said upper and lower arms are moveable between an open position and a closed position, wherein when said upper and lower arms are in the closed position said marking device is adapted to generate a mark on the external surface outside the surgical opening each time one of said surgical fasteners is dispensed inside the surgical opening, and wherein each of the marks mirror the location of each of said surgical fasteners dispensed inside the surgical opening.

17. The device as claimed in claim 16, wherein said surgical fastener dispenser further comprises an insertion fork that engages a leading one of said surgical fasteners for dispensing said leading surgical fastener through said surgical fastener dispenser opening.

18. The device as claimed in claim 17, wherein said marker is pivotally secured to the distal end of said upper arm and is adapted to contact the external surface each time one of said surgical fasteners is dispensed into the tissue inside the surgical opening for providing a visible pattern of markings on the external surface indicating the number and location of each said surgical fastener dispensed into the tissue inside the surgical opening.

19. The device as claimed in claim 18, further comprising an actuator coupled with said upper and lower arms for selectively moving said upper and lower arms between an open position in which said marking assembly is spaced from said surgical fastener dispenser and a closed position in which the tissue is clamped between said marking assembly and said surgical fastener dispenser, wherein said actuator comprises
a hand grip secured to said lower arm,
a trigger mounted on said lower arm and linked with said upper arm, wherein said trigger is adapted for being pulled toward said hand grip for moving said arms into the closed position, and moving away from said hand grip for moving said arms into the open position, and
a trigger return spring coupled with said trigger for normally urging said trigger to move away from said hand grip.

20. A device for dispensing surgical fasteners into tissue inside a surgical opening while simultaneously generating marks on an external surface outside the surgical opening, said device comprising:
a lower arm having a proximal end and a distal end including a surgical fastener dispenser opening adapted for dispensing surgical fasteners;
an upper arm coupled with said lower arm and having a distal end that opposes said surgical fastener dispenser opening at the distal end of said lower arm;
a marking assembly secured to the distal end of said upper arm and opposing said surgical fastener dispenser opening at the distal end of said lower arm;
wherein the distal ends of said upper and lower arms are moveable between an open position and a closed position, wherein when said upper and lower arms are in the closed position said marking device is adapted to generate a mark on the external surface outside the surgical opening each time one of said surgical fasteners is dispensed inside the surgical opening, and wherein each of the marks mirror the location of each of said surgical fasteners dispensed inside the surgical opening;
a surgical fastener dispenser secured to the distal end of said lower arm, wherein said surgical fastener dispenser includes said surgical fastener dispenser opening, said surgical fastener dispenser comprising
a support tray having a proximal end connected with the distal end of said lower arm, and a distal end including an insertion fork that extends along a predetermined axis relative to a longitudinal axis of said lower arm;
a cartridge body overlying said support tray, said cartridge body having a proximal end pivotally connected with the proximal end of said support tray, and a distal end freely moveable relative to the distal end of said support tray, said top surface of said cartridge body extending between the proximal and distal ends of said cartridge body and said dispenser opening being in alignment with said insertion fork;
a cartridge body return spring in contact with said cartridge body and said support tray for normally urging the distal end of said cartridge body away from said support tray; and
a plurality of surgical fasteners arrayed in a series for being dispensed one at a time from said dispenser opening, wherein each of said surgical fasteners has an insertion end oriented toward said top surface of said cartridge body.

\* \* \* \* \*